United States Patent
Panka

(10) Patent No.: US 10,947,597 B2
(45) Date of Patent: Mar. 16, 2021

(54) METHODS FOR DETECTING BRAF IN CANCER

(71) Applicant: BETH ISRAEL DEACONESS MEDICAL CENTER, INC, Boston, MA (US)

(72) Inventor: David J. Panka, Boston, MA (US)

(73) Assignee: BETH ISRAEL DEACONESS MEDICAL CENTER, INC., Boston, MA (US)

( * ) Notice: Subject to any disclaimer, the term of this patent is extended or adjusted under 35 U.S.C. 154(b) by 0 days.

(21) Appl. No.: 15/523,179

(22) PCT Filed: Oct. 29, 2015

(86) PCT No.: PCT/US2015/058119
§ 371 (c)(1),
(2) Date: Apr. 28, 2017

(87) PCT Pub. No.: WO2016/069928
PCT Pub. Date: May 6, 2016

(65) Prior Publication Data
US 2017/0362661 A1 Dec. 21, 2017

Related U.S. Application Data

(60) Provisional application No. 62/093,306, filed on Dec. 17, 2014, provisional application No. 62/073,815, filed on Oct. 31, 2014.

(51) Int. Cl.
| | | |
|---|---|---|
| *C12Q 1/68* | (2018.01) | |
| *C12Q 1/6886* | (2018.01) | |
| *A61K 31/437* | (2006.01) | |
| *A61K 31/506* | (2006.01) | |
| *A61K 31/519* | (2006.01) | |

(52) U.S. Cl.
CPC .......... *C12Q 1/6886* (2013.01); *A61K 31/437* (2013.01); *A61K 31/506* (2013.01); *A61K 31/519* (2013.01); *C12Q 2600/106* (2013.01); *C12Q 2600/118* (2013.01); *C12Q 2600/156* (2013.01); *C12Q 2600/158* (2013.01)

(58) Field of Classification Search
None
See application file for complete search history.

(56) References Cited

FOREIGN PATENT DOCUMENTS

| CN | 102154480 A | 8/2011 |
|---|---|---|
| EP | 2439531 A2 | 4/2012 |
| WO | 2014055775 A1 | 4/2014 |

OTHER PUBLICATIONS

Panka et al; Melanoma Res; vol. 20; pp. 401-407; Oct. 2010.*
Panka, D.J. et al., "An inexpensive, specific and highly sensitive protocol to detect the Braf V600E mutation in melanoma tumor biopsies and blood," Melanoma Res., 2010: 20(5): 407-407. doi. 10.1097/CMR.0b013e32833d8d48, p. 1-12, specicially abstract, p. 2-5.
Chapman, P.B., "Improved survival with vemurafenib in melanoma with BRAF V600E mutation," N. Engl. J. Med., 2011, 364:2507-2516, especially p. 2509, col. 1, paragraph 4.
International Search Report and Written Opinion in corresponding PCT/US2015/058119, dated Jan. 21, 2016 (6 pages).
Fusi et al., "Enhanced detection of-mutants by pre-PCR cleavage of wild-type sequences revealed circulating melanoma cells heterogeneity," European Journal of Cancer, Apr. 11, 2011, vol. 47, No. 13, pp. 1971-1976.
Huggett et al., "Real-time RT-PCR normalisation; strategies and considerations," Genes and Immunity, Apr. 1, 2005, vol. 6, No. 4, pp. 279-284.
Panka et al., "Clinical utility of a blood-based BRAF V600E mutation assay in melanoma," Molecular Cancer Therapeutics, Dec. 2014, vol. 13, Iss. 12, pp. 3210-3218.
Schnittger et al., "Abstract 3674: Development and Validation of a Real Time Quantification Assay to Detect and Monitor BRAFV600E—Mutations in Hairy Cell Leukemia," Blood, Nov. 18, 2011, vol. 118, No. 21, pp. 1570-1571, & 53rd Annual Meeting and Exposition of the American-Society-of-Hematology (ASH), San Diego, CA, USA, Dec. 10-13, 2011.
Schnittger et al., "Development and validation of a real-time quantification assay to detect and monitor BRAFV600E mutations in hairy cell leukemia," Blood, Mar. 29, 2012, vol. 119, No. 13, pp. 3151-3154.
Udvardi et al., "Eleven Golden Rules of Quantitative RT-PCR," The Plant Cell, Jul. 22, 2008, vol. 20, No. 7, pp. 1736-1737.
Extended European Search Report issued in corresponding European Patent Application No. 15854605.1, dated Sep. 19, 2018 (18 pages).
Examination Report issued in corresponding Australian Patent Application No. 2015339137, dated Jul. 2, 2020 (7 pages).

* cited by examiner

Primary Examiner — Jehanne S Sitton
(74) Attorney, Agent, or Firm — Melissa Hunter-Ensor; Jana E. Harris; Greenberg Traurig, LLP

(57) ABSTRACT

The invention features compositions and methods for detecting and quantifying $BRAF^{V600E}$ in a sample of a subject. In particular embodiments, the invention provides a highly sensitive and precise quantitative method for diagnosis, post-operative surveillance, and monitoring evidence of disease over time in the adjuvant setting (i.e. treatment with BRAF-inhibitors).

14 Claims, 24 Drawing Sheets
Specification includes a Sequence Listing.

Pre-operative BRAF V600E blood levels isolated from patients undergoing thyroid surgery for benign (white) and malignant (black) disease. Data are presented as picograms of circulating BRAF V600E determined from a standard curve.

FIG. 6

| Diagnosis | N = 46 |
|---|---|
| *Malignant* | |
| PTC (67% BRAG+) | 36 |
| *Benign* | |
| Adenoma | 3 |
| Nodular hyperplasia | 7 |

Exact match of forward oligo and probe in BRAF V600E

V600E

Single base mis-match of forward oligo and probe in BRAF WT

WT

SEQUENCE LISTING

```
<160> NUMBER OF SEQ ID NOS: 6

<210> SEQ ID NO 1
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1
ccatatcatt gagaccaaat ttgagatg                                       28
```

```
<210> SEQ ID NO 2
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 2
ggcactctgc cattaatctc ttcatgg                                           27

<210> SEQ ID NO 3
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3
acgccaagtc aatcatccac agag                                              24

<210> SEQ ID NO 4
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4
ccgtacctta ctgagatctg gagacagg                                          28

<210> SEQ ID NO 5
<211> LENGTH: 766
<212> TYPE: PRT
<213> ORGANISM: Homo sapiens

<400> SEQUENCE: 5

Met Ala Ala Leu Ser Gly Gly Gly Gly Gly Ala Glu Pro Gly Gln
1               5                   10                  15

Ala Leu Phe Asn Gly Asp Met Glu Pro Glu Ala Gly Ala Gly Ala Gly
            20                  25                  30

Ala Ala Ala Ser Ser Ala Ala Asp Pro Ala Ile Pro Glu Glu Val Trp
        35                  40                  45

Asn Ile Lys Gln Met Ile Lys Leu Thr Gln Glu His Ile Glu Ala Leu
    50                  55                  60

Leu Asp Lys Phe Gly Gly Glu His Asn Pro Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95

Gln Gln Leu Leu Glu Ser Leu Gly Asn Gly Thr Asp Phe Ser Val Ser
            100                 105                 110

Ser Ser Ala Ser Met Asp Thr Val Thr Ser Ser Ser Ser Ser Ser Leu
        115                 120                 125

Ser Val Leu Pro Ser Ser Leu Ser Val Phe Gln Asn Pro Thr Asp Val
    130                 135                 140

Ala Arg Ser Asn Pro Lys Ser Pro Gln Lys Pro Ile Val Arg Val Phe
145                 150                 155                 160
```

```
Leu Pro Asn Lys Gln Arg Thr Val Pro Ala Arg Cys Gly Val Thr
                165                 170                 175

Val Arg Asp Ser Leu Lys Lys Ala Leu Met Met Arg Gly Leu Ile Pro
                180                 185                 190

Glu Cys Cys Ala Val Tyr Arg Ile Gln Asp Gly Glu Lys Lys Pro Ile
                195                 200                 205

Gly Trp Asp Thr Asp Ile Ser Trp Leu Thr Gly Glu Glu Leu His Val
210                 215                 220

Glu Val Leu Glu Asn Val Pro Leu Thr Thr His Asn Phe Val Arg Lys
225                 230                 235                 240

Thr Phe Phe Thr Leu Ala Phe Cys Asp Phe Cys Arg Lys Leu Leu Phe
                245                 250                 255

Gln Gly Phe Arg Cys Gln Thr Cys Gly Tyr Lys Phe His Gln Arg Cys
                260                 265                 270

Ser Thr Glu Val Pro Leu Met Cys Val Asn Tyr Asp Gln Leu Asp Leu
                275                 280                 285

Leu Phe Val Ser Lys Phe Phe Glu His His Pro Ile Pro Gln Glu Glu
                290                 295                 300

Ala Ser Leu Ala Glu Thr Ala Leu Thr Ser Gly Ser Ser Pro Ser Ala
305                 310                 315                 320

Pro Ala Ser Asp Ser Ile Gly Pro Gln Ile Leu Thr Ser Pro Ser Pro
                325                 330                 335

Ser Lys Ser Ile Pro Ile Pro Gln Pro Phe Arg Pro Ala Asp Glu Asp
                340                 345                 350

His Arg Asn Gln Phe Gly Gln Arg Asp Arg Ser Ser Ser Ala Pro Asn
                355                 360                 365

Val His Ile Asn Thr Ile Glu Pro Val Asn Ile Asp Asp Leu Ile Arg
                370                 375                 380

Asp Gln Gly Phe Arg Gly Asp Gly Gly Ser Thr Thr Gly Leu Ser Ala
385                 390                 395                 400

Thr Pro Pro Ala Ser Leu Pro Gly Ser Leu Thr Asn Val Lys Ala Leu
                405                 410                 415

Gln Lys Ser Pro Gly Pro Gln Arg Glu Arg Lys Ser Ser Ser Ser Ser
                420                 425                 430

Glu Asp Arg Asn Arg Met Lys Thr Leu Gly Arg Arg Asp Ser Ser Asp
                435                 440                 445

Asp Trp Glu Ile Pro Asp Gly Gln Ile Thr Val Gly Gln Arg Ile Gly
                450                 455                 460

Ser Gly Ser Phe Gly Thr Val Tyr Lys Gly Lys Trp His Gly Asp Val
465                 470                 475                 480

Ala Val Lys Met Leu Asn Val Thr Ala Pro Thr Pro Gln Gln Leu Gln
                485                 490                 495

Ala Phe Lys Asn Glu Val Gly Val Leu Arg Lys Thr Arg His Val Asn
                500                 505                 510

Ile Leu Leu Phe Met Gly Tyr Ser Thr Lys Pro Gln Leu Ala Ile Val
                515                 520                 525

Thr Gln Trp Cys Glu Gly Ser Ser Leu Tyr His His Leu His Ile Ile
                530                 535                 540

Glu Thr Lys Phe Glu Met Ile Lys Leu Ile Asp Ile Ala Arg Gln Thr
545                 550                 555                 560

Ala Gln Gly Met Asp Tyr Leu His Ala Lys Ser Ile Ile His Arg Asp
                565                 570                 575
```

```
Leu Lys Ser Asn Asn Ile Phe Leu His Glu Asp Leu Thr Val Lys Ile
                580                 585                 590
Gly Asp Phe Gly Leu Ala Thr Val Lys Ser Arg Trp Ser Gly Ser His
            595                 600                 605
Gln Phe Glu Gln Leu Ser Gly Ser Ile Leu Trp Met Ala Pro Glu Val
        610                 615                 620
Ile Arg Met Gln Asp Lys Asn Pro Tyr Ser Phe Gln Ser Asp Val Tyr
625                 630                 635                 640
Ala Phe Gly Ile Val Leu Tyr Glu Leu Met Thr Gly Gln Leu Pro Tyr
                645                 650                 655
Ser Asn Ile Asn Asn Arg Asp Gln Ile Ile Phe Met Val Gly Arg Gly
            660                 665                 670
Tyr Leu Ser Pro Asp Leu Ser Lys Val Arg Ser Asn Cys Pro Lys Ala
        675                 680                 685
Met Lys Arg Leu Met Ala Glu Cys Leu Lys Lys Lys Arg Asp Glu Arg
690                 695                 700
Pro Leu Phe Pro Gln Ile Leu Ala Ser Ile Glu Leu Leu Ala Arg Ser
705                 710                 715                 720
Leu Pro Lys Ile His Arg Ser Ala Ser Glu Pro Ser Leu Asn Arg Ala
                725                 730                 735
Gly Phe Gln Thr Glu Asp Phe Ser Leu Tyr Ala Cys Ala Ser Pro Lys
            740                 745                 750
Thr Pro Ile Gln Ala Gly Gly Tyr Gly Ala Phe Pro Val His
        755                 760                 765

<210> SEQ ID NO 6
<211> LENGTH: 2949
<212> TYPE: DNA
<213> ORGANISM: Homo sapiens

<400> SEQUENCE: 6
```

| | | | | | |
|---|---|---|---|---|---|
| cgcctcccttt | cccctccccc | gcccgacagc | ggccgctcgg | gccccggctc | tcggttataa | 60 |
| gatggcggcg | ctgagcggtg | gcggtggtgg | cggcgcggag | ccgggccagg | ctctgttcaa | 120 |
| cggggacatg | gagcccgagg | ccggcgccgg | cgccggcgcc | gcggcctctt | cggctgcgga | 180 |
| ccctgccatt | ccggaggagg | tgtggaatat | caaacaaatg | attaagttga | cacaggaaca | 240 |
| tatagaggcc | ctattggaca | aatttggtgg | ggagcataat | ccaccatcaa | tatatctgga | 300 |
| ggcctatgaa | gaatacacca | gcaagctaga | tgcactccaa | caaagagaac | aacagttatt | 360 |
| ggaatctctg | ggaacggaa | ctgattttc | tgtttctagc | tctgcatcaa | tggataccgt | 420 |
| tacatcttct | tcctcttcta | gcctttcagt | gctaccttca | tctctttcag | tttttcaaaa | 480 |
| tcccacagat | gtggcacgga | gcaaccccaa | gtcaccacaa | aaacctatcg | ttagagtctt | 540 |
| cctgcccaac | aaacagagga | cagtggtacc | tgcaaggtgt | ggagttacag | tccgagacag | 600 |
| tctaaagaaa | gcactgatga | tgagaggtct | aatcccagag | tgctgtgctg | tttacagaat | 660 |
| tcaggatgga | gagaagaaac | caattggttg | ggacactgat | atttcctggc | ttactggaga | 720 |
| agaattgcat | gtggaagtgt | tggagaatgt | tccacttaca | acacacaact | tgtacgaaaa | 780 |
| aacgttttc | accttagcat | tttgtgactt | ttgtcgaaag | ctgcttttcc | agggtttccg | 840 |
| ctgtcaaaca | tgtggttata | aatttcacca | gcgttgtagt | acagaagttc | cactgatgtg | 900 |
| tgttaattat | gaccaacttg | atttgctgtt | tgtctccaag | ttctttgaac | caccccaat | 960 |
| accacaggaa | gaggcgtcct | tagcagagac | tgccctaaca | tctggatcat | ccccttccgc | 1020 |
| acccgcctcg | gactctattg | gccccaaat | tctcaccagt | ccgtctcctt | caaaatccat | 1080 |

-continued

```
tccaattcca cagcccttcc gaccagcaga tgaagatcat cgaaatcaat ttgggcaacg    1140
agaccgatcc tcatcagctc ccaatgtgca tataaacaca atagaacctg tcaatattga    1200
tgacttgatt agagaccaag gatttcgtgg tgatggagga tcaaccacag gtttgtctgc    1260 tacccccct gcctcattac ctggctcact aactaacgtg aaagccttac agaaatctcc     1320
aggacctcag cgagaaagga agtcatcttc atcctcagaa gacaggaatc gaatgaaaac    1380
acttggtaga cgggactcga gtgatgattg ggagattcct gatgggcaga ttacagtggg    1440
acaaagaatt ggatctggat catttggaac agtctacaag ggaaagtggc atggtgatgt    1500
ggcagtgaaa atgttgaatg tgacagcacc tacacctcag cagttacaag ccttcaaaaa    1560
tgaagtagga gtactcagga aaacacgaca tgtgaatatc ctactcttca tgggctattc    1620
cacaaagcca caactggcta ttgttaccca gtggtgtgag ggctccagct tgtatcacca    1680
tctccatatc attgagacca aatttgagat gatcaaactt atagatattg cacgacagac    1740
tgcacagggc atggattact tacacgccaa gtcaatcatc cacagagacc tcaagagtaa    1800
taatatattt cttcatgaag acctcacagt aaaaataggt gattttggtc tagctacagt    1860
gaaatctcga tggagtgggt cccatcagtt tgaacagttg tctggatcca ttttgtggat    1920
ggcaccagaa gtcatcagaa tgcaagataa aaatccatac agctttcagt cagatgtata    1980
tgcatttgga attgttctgt atgaattgat gactggacag ttaccttatt caaacatcaa    2040
caacagggac cagataattt ttatggtggg acgaggatac ctgtctccag atctcagtaa    2100
ggtacggagt aactgtccaa aagccatgaa gagattaatg gcagagtgcc tcaaaaagaa    2160
aagagatgag agaccactct ttccccaaat tctcgcctct attgagctgc tggcccgctc    2220
attgccaaaa attcaccgca gtgcatcaga accctccttg aatcgggctg gtttccaaac    2280
agaggatttt agtctatatg cttgtgcttc tccaaaaaca cccatccagg caggggata    2340 tggtgcgttt cctgtccact gaaacaaatg agtgagagag ttcaggagag tagcaacaaa    2400
aggaaaataa atgaacatat gtttgcttat atgttaaatt gaataaaata ctctcttttt    2460
ttttaaggtg aaccaaagaa cacttgtgtg gttaaagact agatataatt tttccccaaa    2520
ctaaaattta tacttaacat tggattttta acatccaagg gttaaaatac atagacattg    2580
ctaaaaattg gcagagcctc ttctagaggc tttactttct gttccgggtt tgtatcattc    2640
acttggttat tttaagtagt aaacttcagt ttctcatgca acttttgttg ccagctatca    2700
catgtccact agggactcca gaagaagacc ctacctatgc ctgtgtttgc aggtgagaag    2760
ttggcagtcg gttagcctgg gttagataag gcaaactgaa cagatctaat ttaggaagtc    2820
agtagaattt aataattcta ttattattct taataatttt tctataacta tttctttta    2880 taacaatttg gaaaatgtgg atgtctttta tttccttgaa gcaataaact aagtttcttt    2940
ttataaaaa                                                            2949
```

METHODS FOR DETECTING BRAF IN CANCER

CROSS-REFERENCE TO RELATED APPLICATIONS

This application is the U.S. national phase application, pursuant to 35 U.S.C. § 371, of PCT international application Ser. No.: PCT/US2015/058119, filed Oct. 29, 2015, designating the United States and published in English, which claims the benefit and priority to U.S. Provisional Application Nos. 62/073,815, filed Oct. 31, 2014, and 62/093,306, filed Dec. 17, 2014, respectively. The entire contents of these applications is hereby incorporated herein by reference.

STATEMENT OF RIGHTS TO INVENTIONS MADE UNDER FEDERALLY SPONSORED RESEARCH

This invention was made with government support under Grant No.: CA93683 awarded by the National Cancer Institute. The government has certain rights in the invention.

BACKGROUND OF THE INVENTION

Approximately 40 percent of people will be diagnosed with cancer at some point during their lifetime. It is generally estimated that thyroid carcinoma comprises approximately 1% of all malignancies. In Europe and the US, about 3 out of 100,000 people develop a thyroid malignancy. Papillary thyroid carcinoma (PTC) is the most common malignant thyroid neoplasm in the US and Europe, and comprises up to 80% of all thyroid malignancies. While thyroid cancer occurs in all age groups, it is most common in the 3rd to 5th decades.

In order to plan the adequate therapeutic strategy, the diagnosis of differentiated thyroid carcinoma should be made preoperatively. In many patients, the diagnosis will be made postoperatively, and a second surgery may be required for complete thyroidectomy and/or lymph node dissection. The risks and complications associated with multiple surgeries could be avoided if reliable, sensitive, and non-invasive methods for preoperative diagnosis were available.

Metastatic melanoma is currently the 5th and 7th most common cancer in American men and women, respectively, and remains one of the few cancers with a rising incidence. Over 9000 people are expected to die in the United States in 2013 from this disease. Recent treatment advances have led to the FDA approval of two BRAF inhibitors, vemurafenib (Zelboraf) and dabrafenib (Tafinlar), a MEK inhibitor, trametinib (Mekinist), and the immunotherapy ipilimumab (Yervoy) for the treatment of patients with advanced melanoma. Unfortunately, resistance to BRAF and MEK inhibitor therapy is common, response to ipilimumab uncommon, and durable response to any therapy infrequent; as such, the overwhelming majority of these patients eventually will die of their disease. Most patients with BRAF mutant disease will be candidates for multiple lines of therapy, but conventional radiographic monitoring to track response and progression fails to identify patients at a point when they can receive benefit from follow on therapy. There is a critical need to develop highly sensitive blood-based biomarkers that could enable better treatment selection and improved monitoring of patients with advanced and high-risk melanoma or thyroid cancer.

SUMMARY OF THE INVENTION

As described below, the present invention features compositions and methods for detecting and quantifying $BRAF^{V600E}$ in a blood sample of a subject (e.g., a subject having thyroid cancer or melanoma). In particular embodiments, the invention provides a highly sensitive and precise quantitative method for diagnosis, post-operative surveillance, and monitoring evidence of disease over time in the adjuvant setting (i.e. treatment with BRAF-inhibitors).

In one aspect, the invention generally features a method for quantitatively detecting thyroid cancer or melanoma containing a $BRAF^{V600E}$ mutation in a subject (e.g., human), the method involving isolating RNA from a biological sample of a subject; using reverse transcriptase to obtain a cDNA; amplifying said cDNA to obtain a BRAF amplicon; and digesting said amplicon with TspR1 to distinguish wild-type BRAF from $BRAF^{V600E}$ and measuring the level of $BRAF^{V600E}$ in the sample, where a level of $BRAF^{V600E}$ greater than about 5 pg quantitatively detects the presence of thyroid cancer or melanoma containing a $BRAF^{V600E}$ mutation in the subject.

In another aspect, the invention provides a method of identifying a subject (e.g., human) as having melanoma or thyroid cancer containing a $BRAF^{V600E}$ mutation, the method involving isolating RNA from a biological sample of a subject; using reverse transcriptase to obtain a cDNA; amplifying said cDNA to obtain a BRAF amplicon; and digesting said amplicon with TspR1 to distinguish wild-type BRAF from $BRAF^{V600E}$ and measuring the level of $BRAF^{V600E}$ in the sample, where a level of $BRAF^{V600E}$ greater than about 5 pg indicates the presence of a $BRAF^{V600E}$ mutation in the melanoma or thyroid cancer in the subject.

In another aspect, the invention provides a method for detecting a $BRAF^{V600E}$ mutation in a biological sample that also contains wild-type BRAF, the method involving isolating RNA from a biological sample of a subject; using reverse transcriptase to obtain a cDNA amplifying said cDNA to obtain a BRAF amplicon; and digesting said amplicon with TspR1 to distinguish wild-type BRAF from $BRAF^{V600E}$ and measuring the level of $BRAF^{V600E}$ in the sample, where a level of $BRAF^{V600E}$ greater than about 5 pg indicates the presence of a $BRAF^{V600E}$ mutation in the biological sample.

In yet another aspect, the invention provides a method for detecting the clinical responsiveness of a thyroid cancer or melanoma containing a $BRAF^{V600E}$ mutation, the method involving isolating RNA from two or more biological samples of a subject, where the samples are obtained prior to and following initiation of anti-cancer therapy; using reverse transcriptase to obtain a cDNA; amplifying said cDNA to obtain a BRAF amplicon; and digesting said amplicon with TspR1 to distinguish wild-type BRAF from $BRAF^{V600E}$ and measuring the level of $BRAF^{V600E}$ in the sample relative to the level present in the sample obtained prior to treatment, where a decrease in the level of $BRAF^{V600E}$ following treatment indicates the clinical responsiveness of the thyroid cancer or melanoma to treatment. In one embodiment, the treatment involves administration of an agent selected from any one or more of vemurafenib, dabrafenib, trametinib, and ipilimumab, or combinations thereof. In another embodiment, the treatment involves surgical resection. In yet another embodiment, the method further involves radiographic imaging, magnetic resonance imaging (MRI), positron emission tomography (PET) scan and/or ultrasound.

In still another aspect, the invention provides a method for detecting resistance and/or relapse in a subject (e.g, human) identified as having thyroid cancer or melanoma containing a $BRAF^{V600E}$ mutation, the method involving isolating RNA from two or more biological samples of a subject, where the samples are obtained prior to and following initiation of anti-cancer therapy; using reverse transcriptase to obtain a cDNA; amplifying said cDNA to obtain a BRAF amplicon;

and digesting said amplicon with TspR1 to distinguish wild-type BRAF from BRAF$^{V600E}$ and measuring the level of BRAF$^{V600E}$ in the sample relative to the level present in a sample obtained at an earlier point in time, where an increase in the level of BRAF$^{V600E}$ is indicative that the thyroid cancer or melanoma has developed resistance and/or has relapsed. In one embodiment, the subject (e.g., human) is identified as in need of a change in treatment regimen. In another embodiment, the sample is a post-operative blood sample. In still another embodiment, the methods further involve correlating relapse using imaging.

In a related aspect, the invention features a method of treating thyroid cancer or melanoma in a pre-selected subject (e.g., human), the method involving administering an effective amount of a BRAF inhibitor to the subject, and where the preselection involves: isolating RNA from a biological sample of a subject; using reverse transcriptase to obtain a cDNA; amplifying said cDNA to obtain a BRAF amplicon; and digesting said amplicon with TspR1 to distinguish wild-type BRAF from BRAF$^{V600E}$ and detecting a level of a BRAF$^{V600E}$ mutation greater than about 5 or 10 pg in the sample. In one embodiment, the subject has a thyroid cancer or melanoma that has acquired resistance to a treatment regimen and/or relapsed.

In yet another aspect, the invention provides a method of selecting treatment for a subject (e.g., human) identified as having thyroid cancer or melanoma, the method involving isolating RNA from a biological sample of a subject; using reverse transcriptase to obtain a cDNA; amplifying said cDNA to obtain a BRAF amplicon; and digesting said amplicon with TspR1 to distinguish wild-type BRAF from BRAF$^{V600E}$ and measuring BRAF$^{V600E}$, where detection of a level of BRAF$^{V600E}$ greater than about 5 or 10 pg in the sample selects the subject for treatment with a BRAF inhibitor.

In still another aspect, the invention provides a method of monitoring treatment in a subject (e.g., human) identified as having thyroid cancer or melanoma, the method involving isolating RNA from two or more biological samples of a subject, where the samples are obtained prior to and following initiation of anti-cancer therapy; using reverse transcriptase to obtain a cDNA; amplifying said cDNA to obtain a BRAF amplicon; and digesting said amplicon with TspR1 to distinguish wild-type BRAF from BRAF$^{V600E}$ and measuring the level of BRAF$^{V600E}$ in the sample relative to the level present in a sample obtained at an earlier point in time, where an increase in the level of BRAF$^{V600E}$ is indicative that the thyroid cancer or melanoma has developed resistance and/or has relapsed, and a decrease indicates that the treatment is effective.

In yet another aspect, the invention provides a method for detecting thyroid cancer in a subject (e.g., human) containing a BRAF$^{V600E}$ mutation, the method involving isolating RNA from a biological sample of a subject; using reverse transcriptase to obtain a cDNA; amplifying said cDNA to obtain a BRAF amplicon; and digesting said amplicon with TspR1 to distinguish wild-type BRAF from BRAF$^{V600E}$ and measuring the level of BRAF$^{V600E}$ in the sample, thereby detecting thyroid cancer in the subject. In one embodiment, a level of BRAF$^{V600E}$ greater than about 5 or 10 pg quantitatively detects the presence of thyroid cancer containing a BRAF$^{V600E}$ mutation in the subject.

In one aspect, the invention provides a kit for quantifying thyroid cancer or melanoma in a blood sample obtained from a subject (e.g., human), the kit containing at least one primer used to obtain a BRAF amplicon, a TspR1 restriction enzyme, and an oligonucleotide control containing a portion of a BRAF polynucleotide encoding a valine or glutamate residue at position 600 of the BRAF protein. In one embodiment, the oligonucleotide control has a known concentration. In another embodiment, the kit contains one or more of the following pairs of oligonucleotides:

```
                                    (SEQ ID NO: 1)
5'(CCATATCATTGAGACCAAATTTGAGATG)3'
and
                                    (SEQ ID NO: 2)
5'(GGCACTCTGCCATTAATCTCTTCATGG)3'
or
                                    (SEQ ID NO: 3)
5'(ACGCCAAGTCAATCATCCACAGAG)3'
and
                                    (SEQ ID NO: 4)
5'(CCGTACCTTACTGAGATCTGGAGACAGG)3'.
```

In various embodiments of any of the previous aspects or any other aspect of the invention delineated herein, the biological sample contains a mixed population of cells. In various embodiments of any of the previous aspects, the mixed population of cells contains an infiltrating stromal and/or immune cell containing a wild-type BRAF allele. In other embodiments of any of the previous aspects, the method detects about 0.1% BRAF$^{V600E}$ mutant cells. In other embodiments of any of the previous aspects, the level of BRAF$^{V600E}$ is greater than about 20 or 30 pg. In still other embodiments of any of the previous aspects, the level of BRAF$^{V600E}$ is greater than about 40, 50, or 100 pg. In various embodiments of the previous aspects, the method is repeated periodically to monitor a therapy, for example, every 3-6 months (e.g., 3, 4, 5, 6 months). In various embodiments of any of the previous aspects, the cDNA is amplified using real time PCR. In one embodiment, the level of BRAF$^{V600E}$ mutation is obtained by comparing the amount detected to a standard curve obtained using a known concentration of cDNA. In various embodiments of any of the previous aspects, the cancer is thyroid cancer. In other embodiments of any of the previous aspects, the biological sample is a blood sample (e.g., containing peripheral blood lymphocytes), a biopsy or a needle biopsy.

Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "BRAF amplicon" is meant an oligonucleotide amplification product that encompasses a portion of a BRAF polynucleotide encoding a valine or glutamate residue at position 600 of the BRAF protein.

By "BRAF protein" is meant a polypeptide having at least 85%, 90%, 95% or 100% identity to NCBI Ref. No. NP_004324 or a fragment thereof that regulates cell proliferation. A wild-type protein is identical or substantially identical to NCBI Ref. No. NP_004324 and comprises a V at amino acid position 600 (bold and underline). An exemplary amino acid sequence is provided below:

(SEQ ID NO: 5)

```
  1 maalsggggg gaepgqalfn gdmepeagag agaaasssaad paipeevwni kqmikltqeh 61 iealldkfgg ehnppsiyle ayeeytskld alqqreqqll eslgngtdfs vsssasmdtv 121 tssssssslsv lpsslsvfqn ptdvarsnpk spqkpivrvf lpnkqrtvvp arcgvtvrds 181 lkkalmmrgl ipeccavyri qdgekkpigw dtdiswltge elhvevlenv pltthnfvrk 241 tfftlafcdf crkllfqgfr cqtcgykfhq rcstevplmc vnydqldllf vskffehhpi 301 pqeeaslaet altsgsspsa pasdsigpqi ltspspsksi pipqpfrpad edhrnqfgqr 361 drsssapnvh intiepvnid dlirdqgfrg dggsttglsa tppaslpgsl tnvkalqksp 421 gpqrerksss ssedrnrmkt lgrrdssddw eipdgqitvg qrigsgsfgt vykgkwhgdv 481 avkmlnvtap tpqqlqafkn evgvlrktrh vnillfmgys tkpqlaivtq wcegsslyhh 541 lhiietkfem iklidiarqt aqgmdylhak siihrdlksn niflhedltv kigdfglatv

601 ksrwsgshqf eqlsgsilwm apevirmqdk npysfqsdvy afgivlyelm tgqlpysnin 661 nrdqiifmvg rgylspdlsk vrsncpkamk rlmaeclkkk rderplfpqi lasiellars 721 lpkihrsase pslnragfqt edfslyacas pktpiqaggy gafpvh
```

By "BRAF" polynucleotide" is meant a nucleic acid sequence encoding a BRAF polypeptide. An exemplary BRAF polynucleotide is provided at NCBI Ref: NM_004333.4, which is reproduced below:

(SEQ ID NO: 6)

```
   1 cgcctccctt ccccctcccc gcccgacagc ggccgctcgg gccccggctc tcggttataa 61 gatggcggcg ctgagcggtg gcggtggtgg cggcgcggag ccgggccagg ctctgttcaa 121 cggggacatg agcccgagg ccggcgcgg cgccggcgcc gcggcctctt cggctgcgga 181 ccctgccatt ccggaggagg tgtggaatat caaacaaatg attaagttga cacaggaaca 241 tatagaggcc ctattggaca aatttggtgg ggagcataat ccaccatcaa tatatctgga 301 ggcctatgaa gaatacacca gcaagctaga tgcactccaa caaagagaac aacagttatt 361 ggaatctctg gggaacggaa ctgattttc tgtttctagc tctgcatcaa tggataccgt 421 tacatcttct cctcttcta gcctttcagt gctaccttca tctctttcag tttttcaaaa 481 tcccacagat gtgcacgga gcaaccccaa gtcaccacaa aaacctatcg ttagagtctt 541 cctgcccaac aaacagagga cagtggtacc tgcaaggtgt ggagttacag tccgagacag 601 tctaaagaaa gcactgatga tgagaggtct aatcccagag tgctgtgctg tttacagaat 661 tcaggatgga gagaagaaac caattggttg ggacactgat atttcctggc ttactggaga 721 agaattgcat gtggaagtgt tggagaatgt tccacttaca acacacaact tgtacgaaaa 781 aacgtttttc accttagcat tttgtgactt ttgtcgaaag ctgcttttcc agggtttccg 841 ctgtcaaaca tgtggttata aatttcacca gcgttgtagt acagaagttc cactgatgtg 901 tgttaattat gaccaacttg atttgctgtt tgtctccaag ttctttgaac accacccaat 961 accacaggaa gaggcgtcct tagcagagac tgccctaaca tctggatcat ccccttccgc 1021 acccgcctcg gactctattg gccccaaat tctcaccagt ccgtctcctt caaaatccat 1081 tccaattcca cagcccttcc gaccagcaga tgaagatcat cgaaatcaat tgggcaacg 1141 agaccgatcc tcatcagctc ccaatgtgca tataaacaca atagaacctg tcaatattga 1201 tgacttgatt agagaccaag gatttcgtgg tgatggagga tcaaccacag gtttgtctgc 1261 tacccccct gcctcattac ctggctcact aactaacgtg aaagccttac agaaatctcc 1321 aggacctcag cgagaaagga gtcatcttc atcctcagaa gacaggaatc gaatgaaaac
```

-continued

```
1381 acttggtaga cgggactcga gtgatgattg ggagattcct gatgggcaga ttacagtggg 1441 acaaagaatt ggatctggat catttggaac agtctacaag ggaaagtggc atggtgatgt 1501 ggcagtgaaa atgttgaatg tgacagcacc tacacctcag cagttacaag ccttcaaaaa 1561 tgaagtagga gtactcagga aaacacgaca tgtgaatatc ctactcttca tgggctattc 1621 cacaaagcca caactggcta ttgttaccca gtggtgtgag ggctccagct tgtatcacca 1681 tctccatatc attgagacca aatttgagat gatcaaactt atagatattg cacgacagac 1741 tgcacagggc atggattact tacacgccaa gtcaatcatc cacagagacc tcaagagtaa 1801 taatatattt cttcatgaag acctcacagt aaaaataggt gattttggtc tagctacagt 1861 gaaatctcga tggagtgggt cccatcagtt tgaacagttg tctggatcca ttttgtggat 1921 ggcaccagaa gtcatcagaa tgcaagataa aaatccatac agctttcagt cagatgtata 1981 tgcatttgga attgttctgt atgaattgat gactggacag ttaccttatt caaacatcaa 2041 caacagggac cagataattt ttatggtggg acgaggatac ctgtctccag atctcagtaa 2101 ggtacggagt aactgtccaa aagccatgaa gagattaatg gcagagtgcc tcaaaagaa 2161 aagagatgag agaccactct ttccccaaat tctcgcctct attgagctgc tggcccgctc 2221 attgccaaaa attcaccgca gtgcatcaga accctccttg aatcgggctg gtttccaaac 2281 agaggatttt agtctatatg cttgtgcttc tccaaaaaca cccatccagg caggggata 2341 tggtgcgttt cctgtccact gaaacaaatg agtgagagag ttcaggagag tagcaacaaa 2401 aggaaaataa atgaacatat gtttgcttat atgttaaatt gaataaaata ctctcttttt 2461 ttttaaggtg aaccaaagaa cacttgtgtg gttaaagact agatataatt tttccccaaa 2521 ctaaaattta tacttaacat tggatttta acatccaagg gttaaaatac atagacattg 2581 ctaaaaattg gcagagcctc ttctagaggc tttactttct gttccgggtt tgtatcattc 2641 acttggttat tttaagtagt aaacttcagt ttctcatgca acttttgttg ccagctatca 2701 catgtccact agggactcca gaagaagacc ctacctatgc ctgtgtttgc aggtgagaag 2761 ttggcagtcg gttagcctgg gttagataag gcaaactgaa cagatctaat ttaggaagtc 2821 agtagaattt aataattcta ttattattct taataatttt tctataacta tttctttta 2881 taacaatttg gaaaatgtgg atgtctttta tttccttgaa gcaataaact aagtttcttt 2941 ttataaaaa
```

Mutations in BRAF are known in the art and described, for example, by Davies et al. Mutations of the BRAF gene in human cancer. Nature 2002; 417:949-54. In one embodiment, a BRAF polypeptide of the invention comprises a V600E mutation.

By "alteration" is meant an increase or decrease. An alteration may be by as little as 1%, 2%, 3%, 4%, 5%, 10%, 20%, 30%, or by 40%, 50%, 60%, or even by as much as 75%, 80%, 90%, or 100%.

By "biologic sample" is meant any tissue, cell, fluid, or other material derived from an organism.

By "clinical responsiveness" is meant that a pathological condition is stabilized or reduced in severity in response to treatment. When a pathological condition fails to respond it is said to be "resistant" to treatment. Return of a pathological condition is typically termed a "relapse."

By "detecting" is meant determining the presence or level of an analyte.

By "diagnostic" is meant any method that identifies the presence of a pathologic condition or characterizes the nature of a pathologic condition (e.g., a cancer). Diagnostic methods differ in their sensitivity and specificity. While a particular diagnostic method may not provide a definitive diagnosis of a condition, it suffices if the method provides a positive indication that aids in diagnosis.

By "immune cell" is meant any cell involved in producing an immune response. Exemplary immune cells include, but are not limited to, granulocytes (e.g., basophils, eosinophils, and neutrophils), mast cell, monocytes, dendritic cells, natural killer cells, B cells, T cells, and macrophages.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "marker" is meant any protein or polynucleotide having an alteration in sequence, expression level or activity that is associated with a disease or disorder. In one embodiment, a mutant or wild-type BRAF sequence is used as a marker of thyroid cancer or melanoma.

By "periodic" is meant at regular intervals. Periodic patient monitoring includes, for example, a schedule of tests that are administered daily, bi-weekly, bi-monthly, monthly, bi-annually, or annually.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "sensitivity" is meant the percentage of subjects with a particular disease that are correctly detected as having the disease.

By "subject" is meant a mammal, including, but not limited to, a human or non-human mammal, such as a bovine, equine, canine, ovine, or feline.

By "specificity" is meant the percentage of subjects without a particular disease who test negative.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 1A shows a cartoon of BRAF's role in the MAP kinase/ERKs signaling pathway. FIG. 1B depicts a bar graph showing pre-operative BRAFV600E blood levels isolated from patients undergoing thyroid surgery for benign (cross-hatched) and malignant (horizontal lines) disease. Data were presented as picograms of circulating $BRAF^{V600E}$ determined from a standard curve. FIG. 1C is a graph showing the survival of $BRAF^{V600E}$ positive subjects vs $BRAF^{V600E}$ negative subjects. FIG. 1D is a table outlining the results of a metadata analysis of studies examining BRAF status.

FIG. 5A shows a schematic of the BRAFV600 assay. FIG. 5B provides a standard curve of the BRAF assay. The equation representative of the best fit line for the $BRAF^{V600E}$ (lower equation) and wild type BRAF (upper equation) are shown. FIG. 5C depicts a bar graph showing BRAF expression levels in individual cell lines including a homozygous $BRAF^{V600E}$ mutant line (A375), two BRAF wild-type lines (786-0, Du145), and a heterozygous line (HT29). FIG. 5D shows a graph of a receiver operator curve (ROC) for stage IV BRAF V600E patients. With AUC of 0.9929, the assay had excellent classification ability for Stage IV melanoma.

FIG. 6 is a table providing the clinical status of 46 subjects assayed for BRAF status. 67% of the subjects that were identified as $BRAF^{V600E}$ positive were confirmed to have malignant thyroid disease.

FIG. 12A is a graph of a PCR where 10 picomoles of each, forward oligo and reverse oligo, was used to detect $BRAF^{V600E}$ in a homozygous $BRAF^{V600E}$ mutant cell line (A375) and a BRAF wild-type cell line (786-0). FIG. 12B is a graph of a PCR where a ratio of 10 forward oligos to 0.3 reverse oligo was used to detect $BRAF^{V600E}$ in A375 and 786-0. FIG. 12C is a graph of a PCR where a ratio of 1 forward oligo to 10 reverse oligos was used to detect $BRAF^{V600E}$ in A375 and 786-0. FIG. 12D is a graph of a PCR where a ratio of 0.3 forward oligo to 10 reverse oligos was used to detect $BRAF^{V600E}$ in A375 and 786-0.

FIG. 13A is a graph showing $BRAF^{V600E}$ level in blood obtained from melanoma patients. FIG. 13B is a graph showing distribution of Log(BRAF) by mutation status. FIG. 13C is a graph showing that $BRAF^{V600E}$ level was higher among patients with Stage IV, BRAF mutant melanoma than in patients with Stage II and III melanoma with a "positive" BRAF level (>4.8 pg; p<0.0001 for each). Statistical comparisons based on linear models with disease stage or mutation status as single predictor. Bonferroni corrections were used to adjust for multiple comparisons.

FIG. 14A provides a bar graph showing BRAF V600E blood levels from stage 3 patients post resection compared to separate tissue analysis. The bar graph represents the blood BRAF V600E level in pg to a maximum level of 5 pg. The tissue BRAF V600E status was indicated by a + or – above each bar. FIG. 14B shows a bar graph describing blood BRAF V600E levels from eight patients pre- and postsurgical resection. All patients were previously determined to be BRAF V600E positive by tissue analysis. FIG. 14C depicts a linear graph showing Kaplan-Meier estimates for overall survival according to quartiles of the distribution of $BRAF^{V600E}$ levels (0-0.27 pg; 0.27-0.45 pg; 0.45-0.67 pg and >0.67 pg).

FIG. 15A is a graph showing data of the response of individual patients to the drug regimen. FIG. 15B is a graph showing mean $BRAF^{V600E}$ levels in response to either vemurafenib or the dabrafenib and trametinib combination. The values in FIG. 15B are relative to pretreatment levels (set as 1.0).

FIG. 16A provides a graph showing blood BRAF V600E levels from 7 patients that were treated with vemurafenib compared to their tumor volume by RECIST. FIG. 16B shows a graph describing blood BRAF V600E levels from 5 patients that were treated with a combination of dabrafenib and trametinib compared to their tumor volume by RECIST. In FIGS. 16A and 16B the BRAF V600E levels paralleled the change in tumor volume during treatment with vemurafenib (7 patients) or dabrafenib and trametinib (5 patients) respectively. FIG. 16C provides a graph showing that the blood BRAF V600E levels increased prior to any increase in tumor volume during treatment with vemurafenib (4 patients) or dabrafenib and trametinib (1 patient) respectively. All data were presented as fold change relative to pretreatment values.

DETAILED DESCRIPTION OF THE INVENTION

As described below, the present invention features compositions and methods for detecting and quantifying $BRAF^{V600E}$ in a blood sample of a subject (e.g., a subject having thyroid cancer or melanoma).

The invention is based, at least in part, on the discovery of a highly sensitive and precise quantitative method capable of detecting pg levels of $BRAF^{V600E}$. Such methods are useful for the diagnosis, post-operative surveillance, and monitoring of thyroid cancer and melanoma over time in the adjuvant setting (i.e. treatment with BRAF-inhibitors).

Figure 1A:
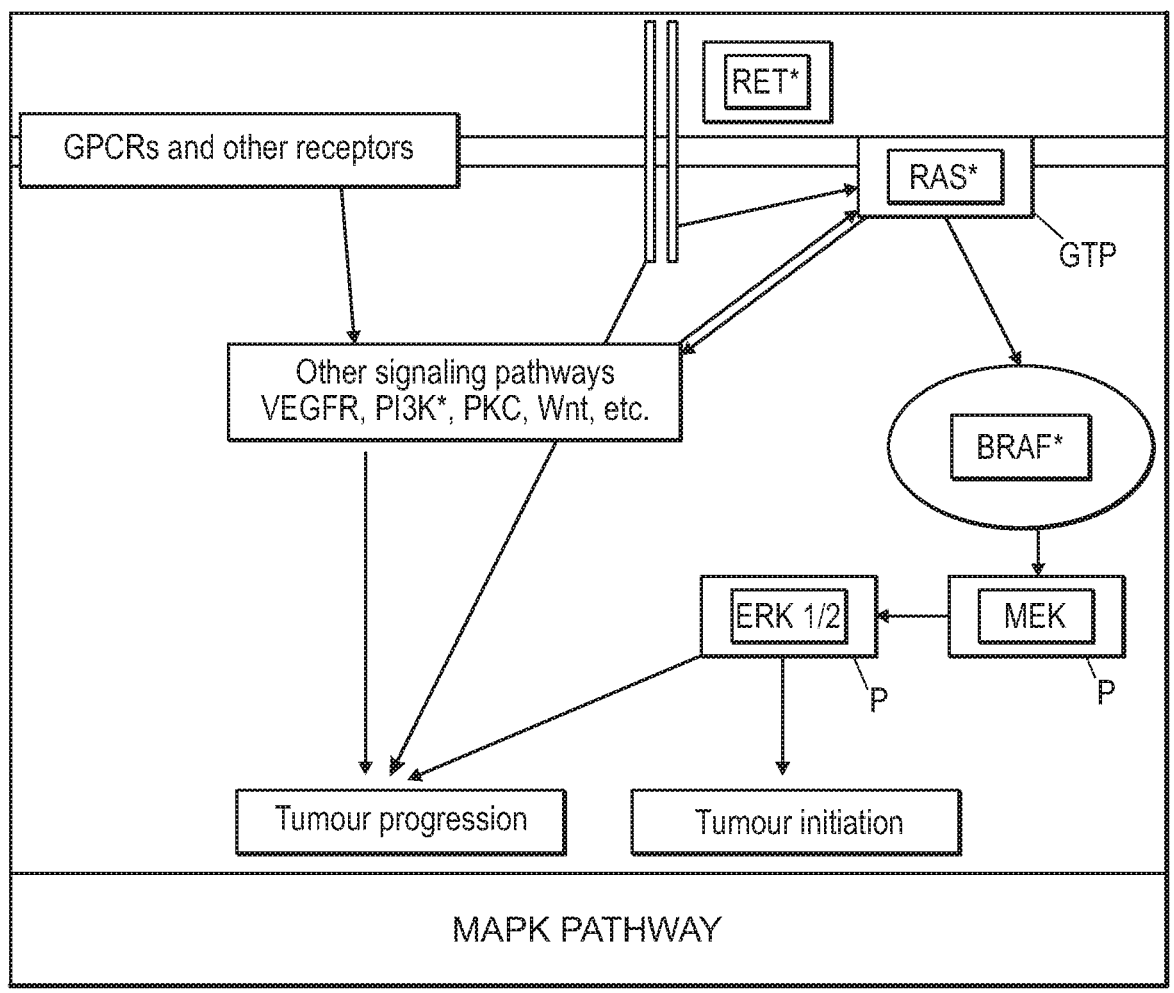
FIGS. 1A-1D provide a cartoon, a bar graph, a linear graph and a table showing that mutant BRAF, a member of the MAP kinase/ERKs pathway, correlates with worse disease outcomes.
Figure 1B:
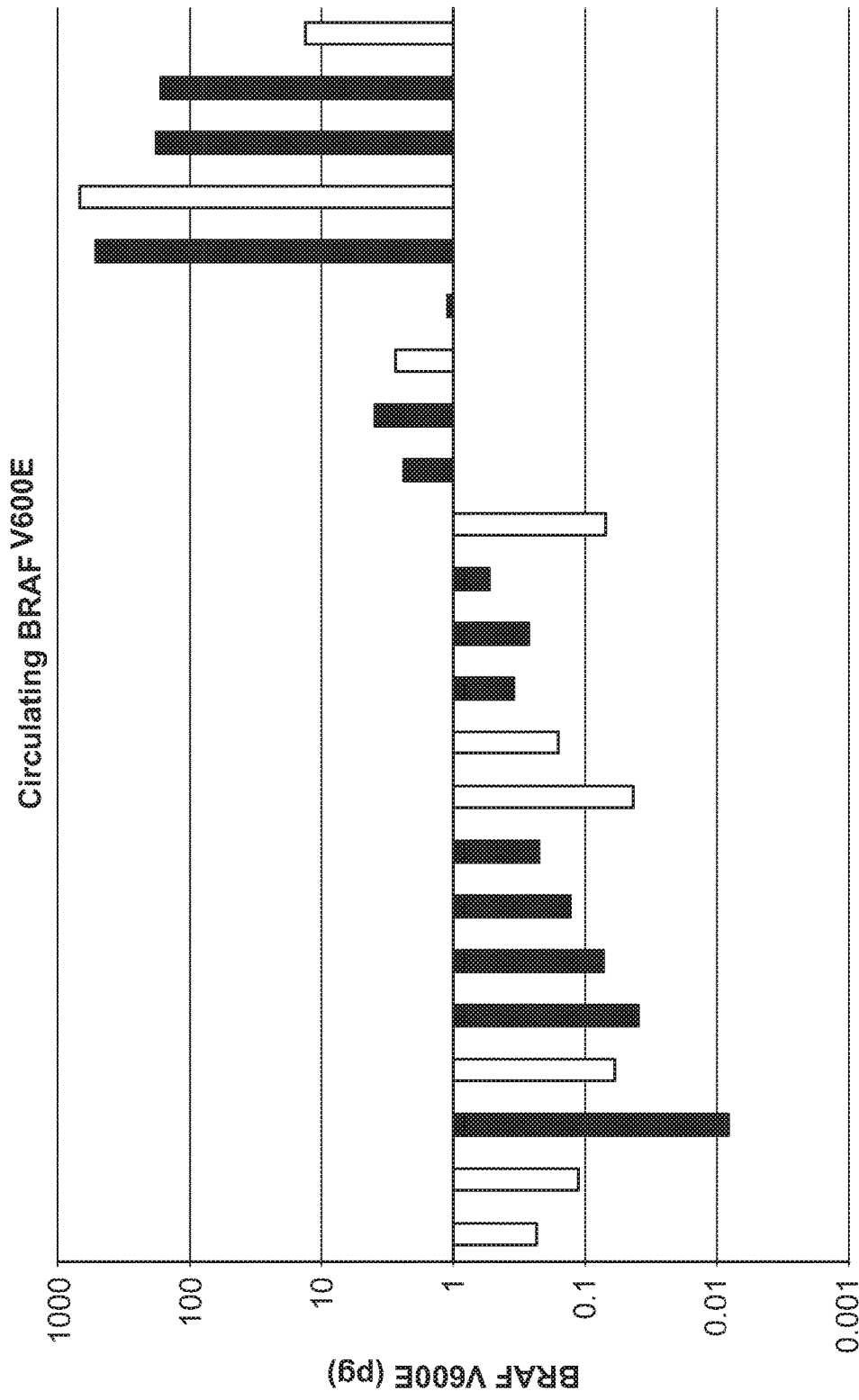

BRAF $BRAF^{V600E}$ is an important driver mutation in thyroid cancer and is found in half of patients with papillary thyroid carcinoma (PTC) (FIGS. 1A and 1B). Detection of this mutation in tumor DNA obtained cytologically or pathologically is useful in work up of nodules or for determining therapeutic options for using novel targeted therapies. Current, standard BRAF testing methods are tissue-based and provide only qualitative data, i.e. positive or negative. The major limitations to these approaches are lack of sensitivity and the need to acquire tissue (either via location of an archived tumor block or fresh biopsy). Most tissue-based assays have the ability to identify one mutant allele in ten or twenty wild-type alleles and thus require tumor specimens that contain approximately 40-50% tumor cellularity to account for heterozygosity and stromal and lymphoid elements typically present in melanoma metastases. While most metastatic tumor biopsies have little trouble meeting this benchmark, analysis of primary melanomas and microscopically involved sentinel nodes are less reliable due to tumor heterogeneity (primary tumors) and/or relative infrequency of tumor cells (sentinel lymph nodes). Further, the identification of an appropriate block or the coordination of biopsy and subsequent analysis delays the start of systemic therapy. In these circumstances, a highly sensitive blood-based assay would provide a superior diagnostic tool. A blood-based assay also would provide serial data about the state of the disease.

For example, patients with resected melanoma have a risk of recurrence and death that ranges from 7-80%. While clinical and pathological staging can narrow the range, it is still broad for each stage of cancer and serial blood testing and imaging is of little value in improving prognostic accuracy. An assay that rises in the setting of disease recurrence would likely enhance the predictive value of imaging and allow for timely diagnosis and treatment of recurrent melanoma. During the treatment of metastatic disease, blood tests that can serve as a surrogate marker of disease status and substitute for more expensive and difficult radiographic imaging, would offer a cost effective option to imaging and allow earlier transition to next line therapy for patients with emerging resistant disease.

The invention provides a highly sensitive and inexpensive, blood based BRAF assay using a unique restriction enzyme site in wild-type BRAF at the V600 position in combination with a Real-Time PCR step that allows for precise quantification of BRAF levels, for example, in patients with stage II, III, and IV melanoma.

As reported in more detail below, wild type Braf has a valine at position 600 coded by a GTG codon. The V600E mutant has a glutamic acid at that position coded by a GAG codon. Blood was collected from patients undergoing thyroidectomy for thyroid disease prior to surgery and up to 4 weeks post-operatively. BRAF status was not known at time of initial collection and no patient had a history of colon cancer or melanoma. Circulating $BRAF^{V600E}$ levels were quantified using a unique restriction enzyme site and a series of PCR amplifications and wild-type BRAF digestions. Extracted RNA was quantified by RT-PCR prior to beginning the assay to normalize all of the samples.

Figure 1C:
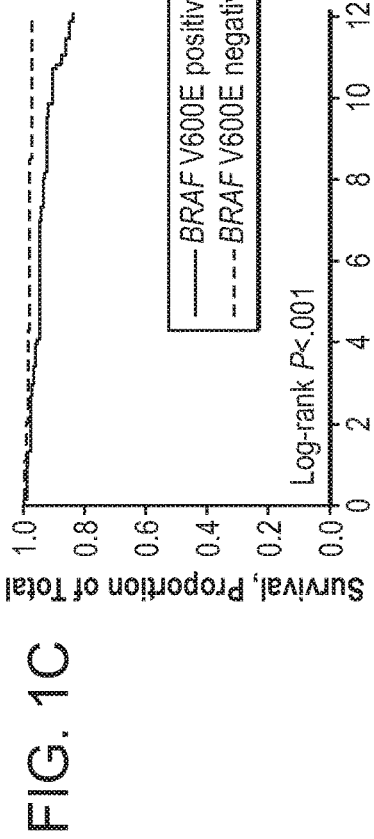
Figure 1D:
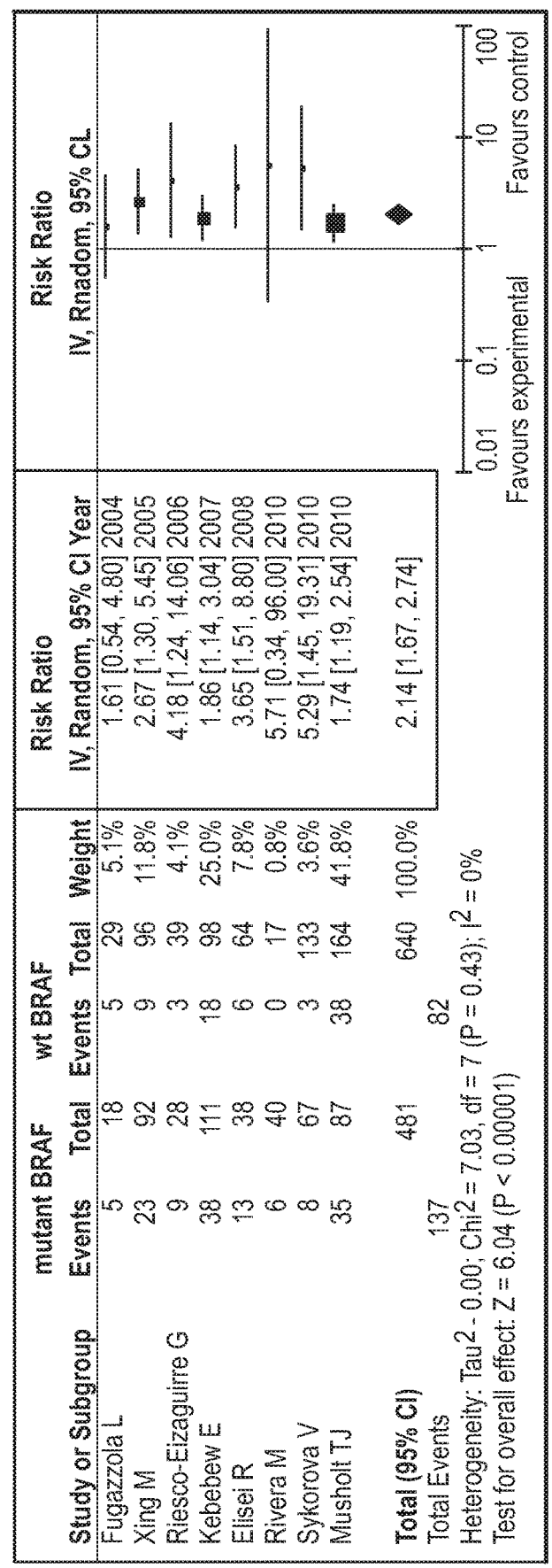
Figure 2:
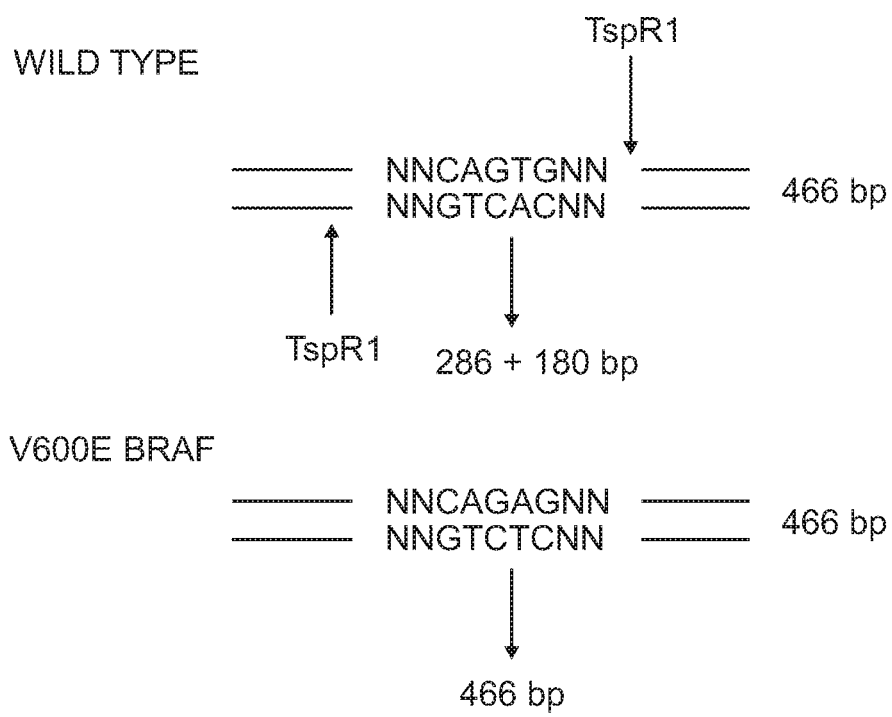
FIG. 2 is a schematic diagram illustrating how the BRAF blood assay discriminated between wild-type and mutant BRAF.

Pre-operative and post-operative blood samples obtained from twenty-three patients undergoing thyroidectomy for benign (nine negative controls) and papillary thyroid carcinoma (PTC) (n=14, AJCC TNM stages I-III) were analyzed. A threshold value of 1.0 picogram as "positive" separated the cohort into two distinct groupings (FIGS. 1C and 1D). Eight of the nine patients with a "positive" test showed a decrease in circulating BRAFV600E post-thyroidectomy. These findings indicate the feasibility of a novel blood assay for detecting circulating mutant BRAF in the blood of patients with papillary thyroid carcinoma. Accordingly, the invention provides a cost-effective method for diagnosis, surveillance in thyroglobulin (Tg)-antibody (Ab) positive patients post-operatively, and in assessing evidence of disease over time in the adjuvant setting (i.e. treatment with BRAF-inhibitors).

Similar methods are applied to subjects with melanoma. Blood BRAFV600E detection and quantification was performed on samples from 128 patients with Stage II (19), III (67), and IV (42) melanoma. Tissue BRAF analysis was performed in all patients with Stage IV disease and in selected patients with Stage II and III disease. Clinical outcomes were correlated to initial BRAF levels as well as BRAF level dynamics. Serial analysis was performed on 17 Stage IV melanoma patients treated with BRAF inhibitor and compared to tumor measurements by RECIST (Response Evaluation Criteria In Solid Tumors). The assay was highly sensitive (96%) and specific (95%) in the Stage IV setting, using a blood level of 4.8 pg as "positive". BRAF levels typically decreased following BRAF inhibitor. A subset of these patients (5) had an increase in BRAF V600E values 42-112 days prior to clinical or radiographic disease progression (PD). From 86 patients with resected, stage II or III melanoma, 39 had evidence of disease relapse (45.3%). Furthermore, BRAF mutation in the blood after surgical resection in these patients was not associated with a difference in relapse risk, though tissue BRAF status was only available for a subset of patients. In summary, the invention provides a highly sensitive and specific, blood-based assay to detect BRAFV600 mutation in patients with melanoma. Accordingly, the invention provides for the use of this assay for diagnostic and prognostic uses, as well as in guiding treatment decisions.

Types of Biological Samples

BRAF status can be measured in a biological fluid or tissue sample. In one embodiment, the tissue sample is a biopsy of the thyroid, melanoma, lymph node, or a metastasis. In one embodiment, the biopsy is a needle biopsy. In another embodiment, the lymph node biopsy is a sentinel lymph node biopsy obtained before, during or after surgery. Biological fluid samples include blood, blood serum, plasma, or any other biological fluid useful in the methods of the invention.

Diagnostic Assays

The present invention provides a number of diagnostic assays that are useful for the identification or characterization of a neoplasia (e.g., thyroid cancer, melanoma). In one embodiment, a neoplasia is characterized by precisely quantifying or determining the BRAF status in a blood sample or biopsy. The methods involve isolating RNA from a blood sample of a subject, using reverse transcriptase to obtain a cDNA; amplifying said cDNA to obtain a BRAF amplicon, and digesting said amplicon with TspR1 to distinguish wild-type BRAF from $BRAF^{V600E}$ and measuring the level of $BRAF^{V600E}$, wherein a level of $BRAF^{V600E}$ greater than about 3, 4, 5, 10, 15, 20, 25, 30, 35, 40, 45, 50, 55, 60 or 65 pg indicates the presence of thyroid cancer or melanoma in the subject. In one embodiment, a level of $BRAF^{V600E}$ greater than about 4.5 pg is indicative of thyroid cancer or melanoma. In another embodiment, a level of $BRAF^{V600E}$ greater than about 4.8 pg is indicative of melanoma harboring the BRAF V600E mutation.

Selection of a Treatment Method and Patient Monitoring

After the BRAF status of a subject is characterized, a method of treatment is selected. Where the level of BRAFV600E is greater than about 4.5 pg the subject is identified as having thyroid cancer. In such case, a number of standard treatment regimens are available. The subject's BRAF status is used in selecting a treatment method.

Thyroid cancers having lower $BRAF^{V600E}$ levels are likely to be susceptible to conservative treatment methods. Conservative treatment methods include, for example, less radical thyroid cancer surgery. For patients undergoing treatment for thyroid cancer, monitoring of the therapy may be carried out. Such periodic patient monitoring involves using diagnostic assays of the invention to measure $BRAF^{V600E}$ levels in blood.

The diagnostic methods of the invention are also useful for monitoring the course of cancer in a patient or for assessing the efficacy of a therapeutic regimen. In one embodiment, the diagnostic methods of the invention are used periodically to monitor the $BRAF^{V600E}$ level. In one example, the neoplasia is characterized using a diagnostic assay of the invention prior to administering therapy. This assay provides a baseline that describes the level of $BRAF^{V600E}$ prior to treatment. Additional $BRAF^{V600E}$ assays are used during the course of therapy to monitor the efficacy of a selected therapeutic regimen. A therapy is identified as efficacious when a diagnostic assay of the invention detects a decrease in $BRAF^{V600E}$ levels relative to the baseline level.

Kits

The invention also provides kits for quantifying thyroid cancer or melanoma in a blood sample obtained from a subject. In various embodiments, the kit includes at least one primer used to amplify a BRAF sequence, and a TspR1 restriction enzyme used to distinguish between a BRAF$^{V600E}$ sequence and wild type BRAF, together with instructions for using the kit to detect thyroid cancer or melanoma.

Preferably, the kit further comprises any one or more of the reagents described in the diagnostic assays described herein. In other embodiments, the instructions include at least one of the following: description of the primer or probe; methods for using the enclosed materials for the diagnosis of a neoplasia; precautions; warnings; indications; clinical or research studies; and/or references. The instructions may be printed directly on the container (when present), or as a label applied to the container, or as a separate sheet, pamphlet, card, or folder supplied in or with the container.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: BRAF⁺ is Correlated with Worse Patient Outcomes

Figure 3:
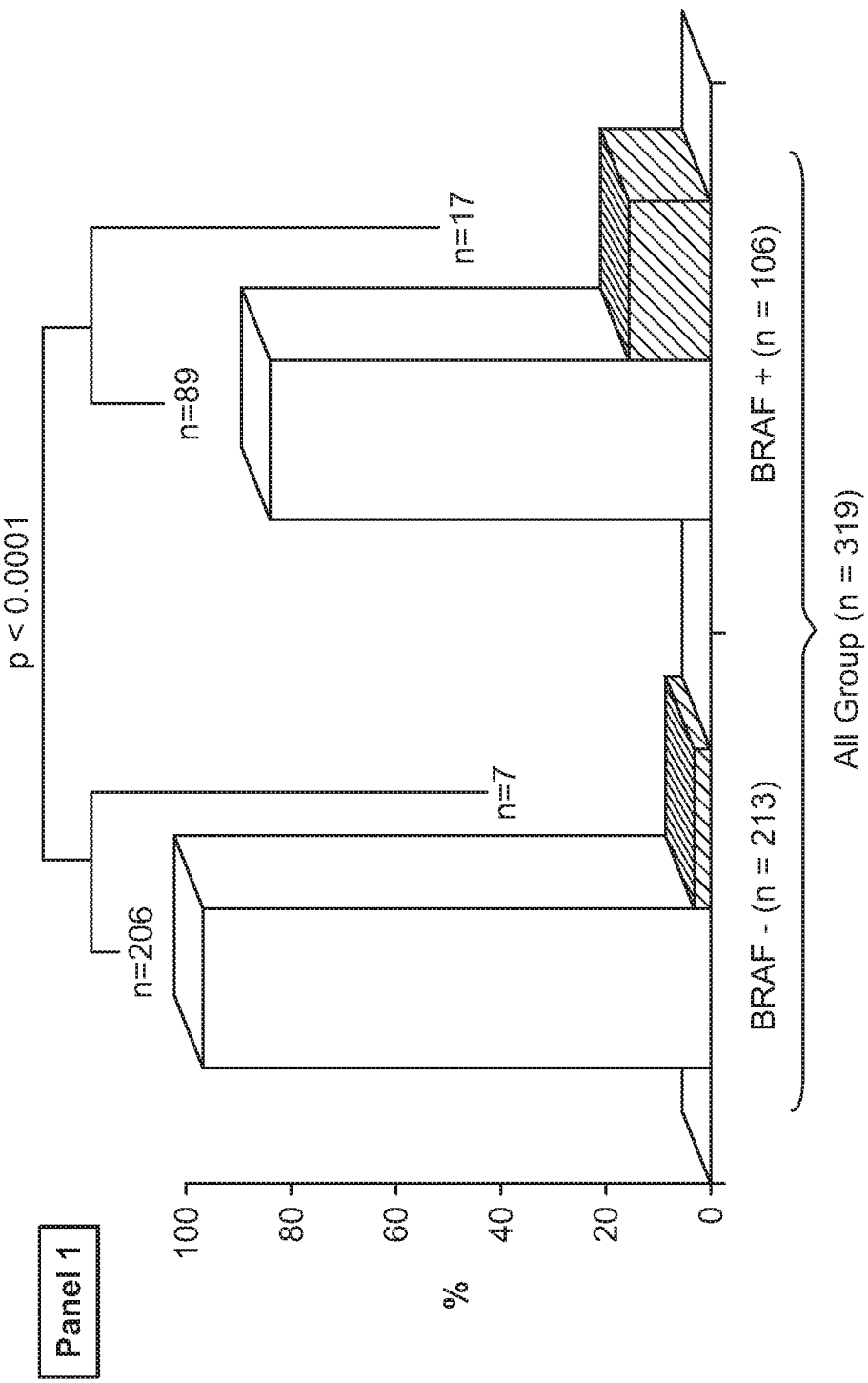
FIG. 3 is a bar graph showing the BRAF status of subjects.
Figure 4:
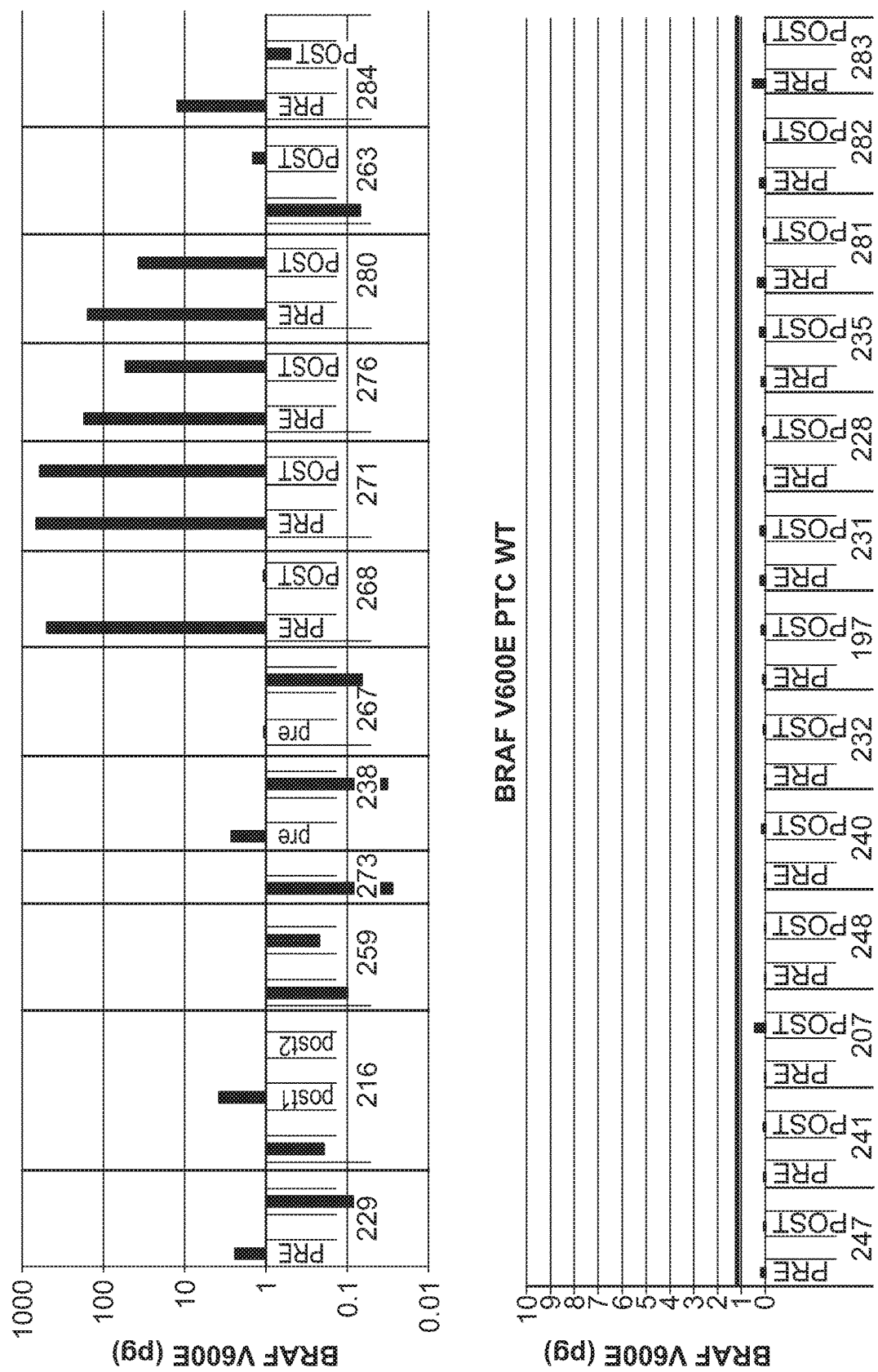
FIG. 4 provides two bar graphs showing how the BRAFV600E assay can detect the $BRAF^{V600E}$ blood levels in the blood from thyroid cancer patients before (top graph) and after (bottom graph) thyroidectomy.

Activating BRAF mutations (BRAF$^{V600E}$) presented in up to ~50% of papillary thyroid carcinoma (PTC). Somatic missense mutation lead to constitutive activation of the MAP kinase pathway (FIG. 1A). BRAF status was characterized in a meta-analysis of 27 studies with 5500 patients (FIGS. 1C and 1D). BRAF+ independently correlated with persistent disease in greater than 300 consecutive patients with Stage I/II disease (FIG. 3). In addition, BRAF status correlated with mortality on univariate analysis (5% in BRAF⁺ vs. 1% in BRAF$^{wt}$, FIGS. 1C and 1D).

Example 2: BRAF Status in Serum Correlates with Cytological Results

BRAF status informs choice of surgical and adjuvant therapy. Tissue is required for conventional BRAF testing. The present invention provides a highly sensitive blood-based BRAF$^{V600E}$ assay for patients that have, are suspected of having, or have a propensity to develop thyroid cancer or melanoma (FIGS. 2, 4 and 5A-5D).

Figure 7:
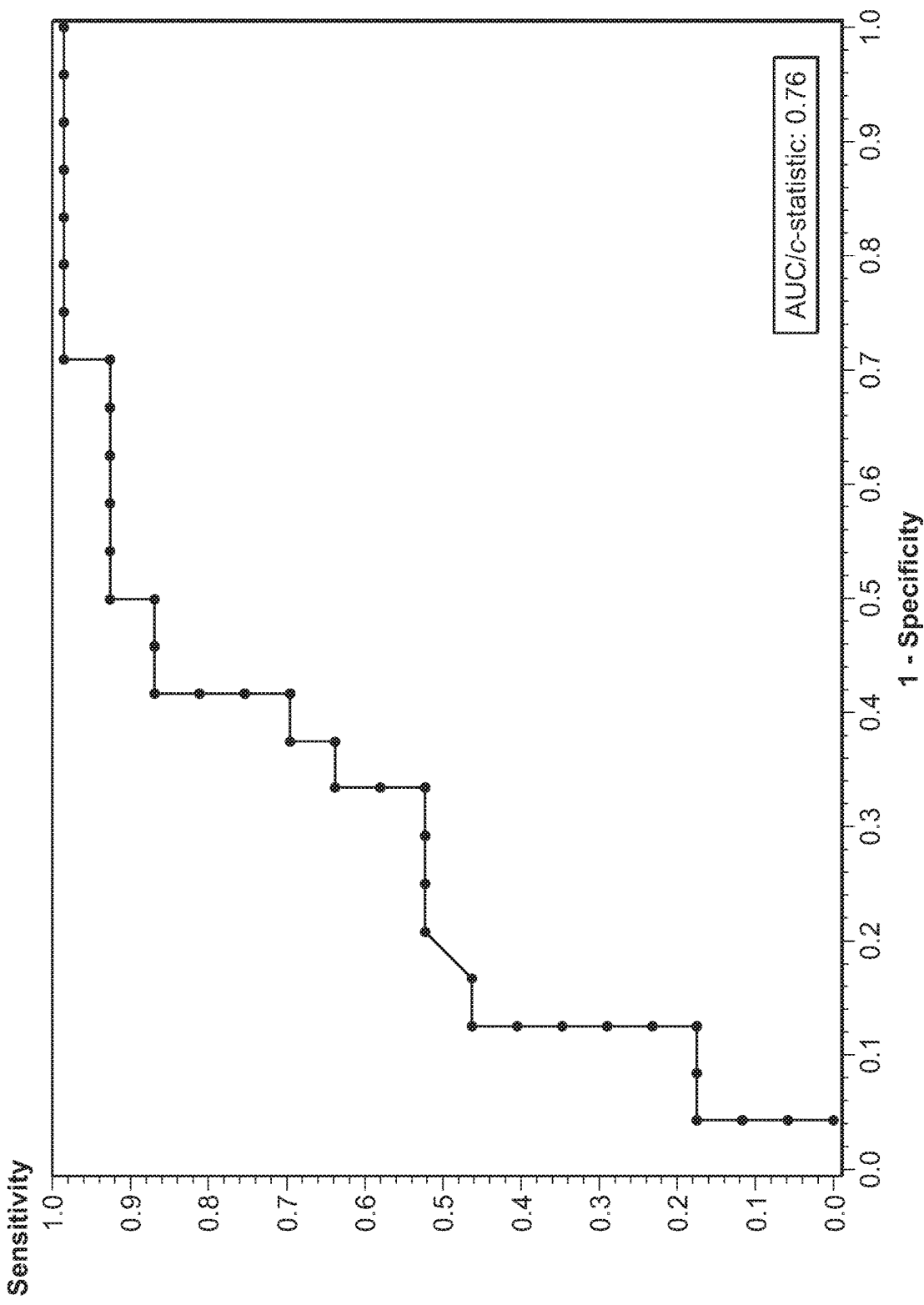
FIG. 7 is a receiver operator curve (ROC) analysis showing the sensitivity and specificity of the BRAFV600E assay in papillary thyroid carcinoma (PTC).

In general, blood was collected from serial patients undergoing thyroidectomy. RNA was isolated from blood followed by two rounds of PCR amplification with a restriction digest specific for wild-type BRAF applied after each PCR. Circulating BRAF$^{V600E}$ levels were compared to BRAF mutation status from surgical pathological assessment with conventional assays. The results of this analysis are shown in FIG. 6. The predictive value of the blood assay for thyroid malignancy is shown in FIG. 7 in an receiver operator curve (ROC) analysis.

Likelihood Ratio=sensitivity/1-specificity
Calculation of Positivity Criterion
Maximizing the likelihood ratio
Consideration of prevalence of "disease" (i.e. BRAF+) and consequences of false negatives and false positives:

$P(D-)*(CTN-CFP)$ $P(D+)*(CTP-CFN)$

Figure 8:
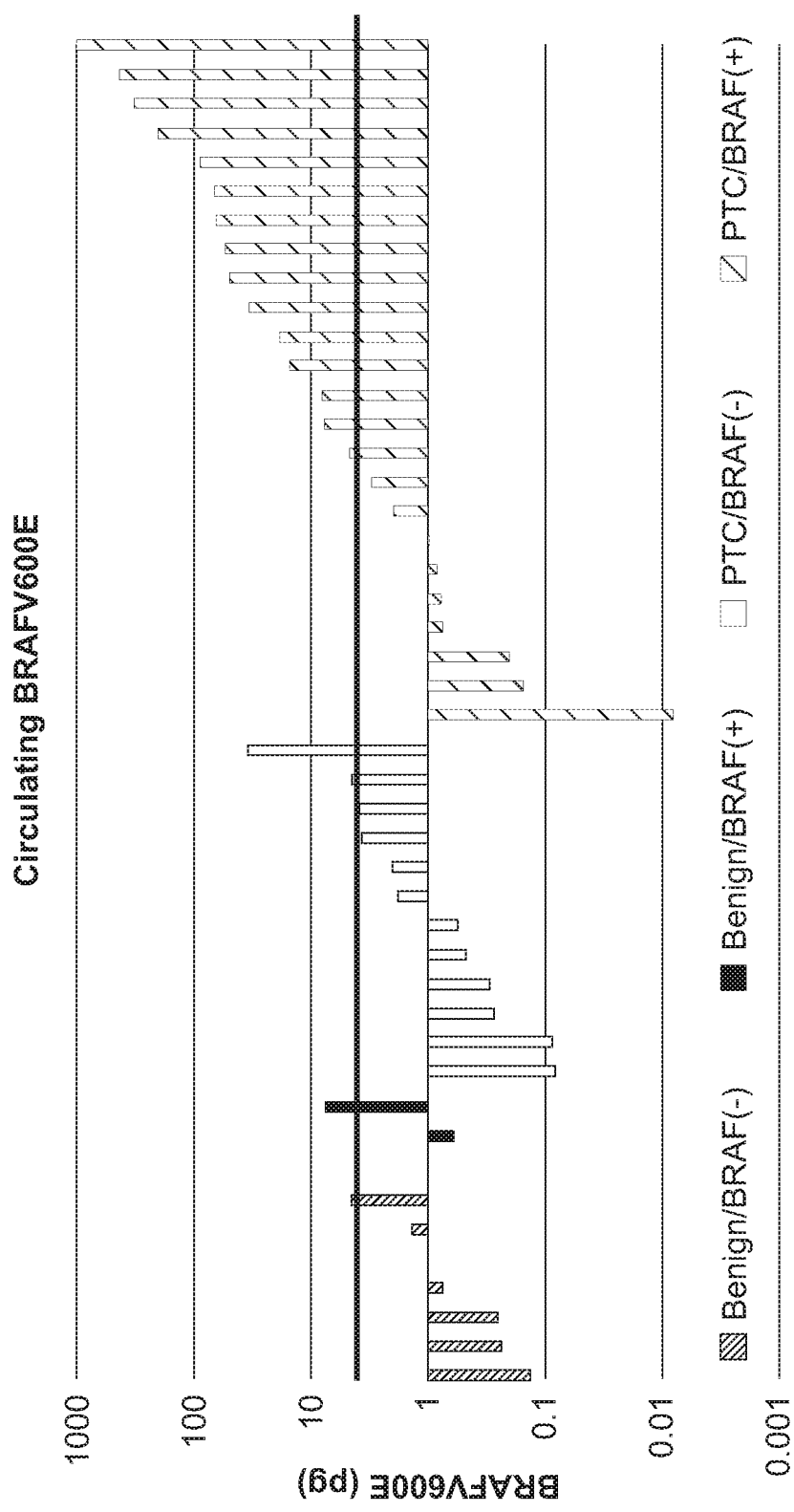
FIG. 8 provides an analysis of BRAF status and tumor malignancy as a function of $BRAF^{V600E}$ level in blood.
Figure 9:
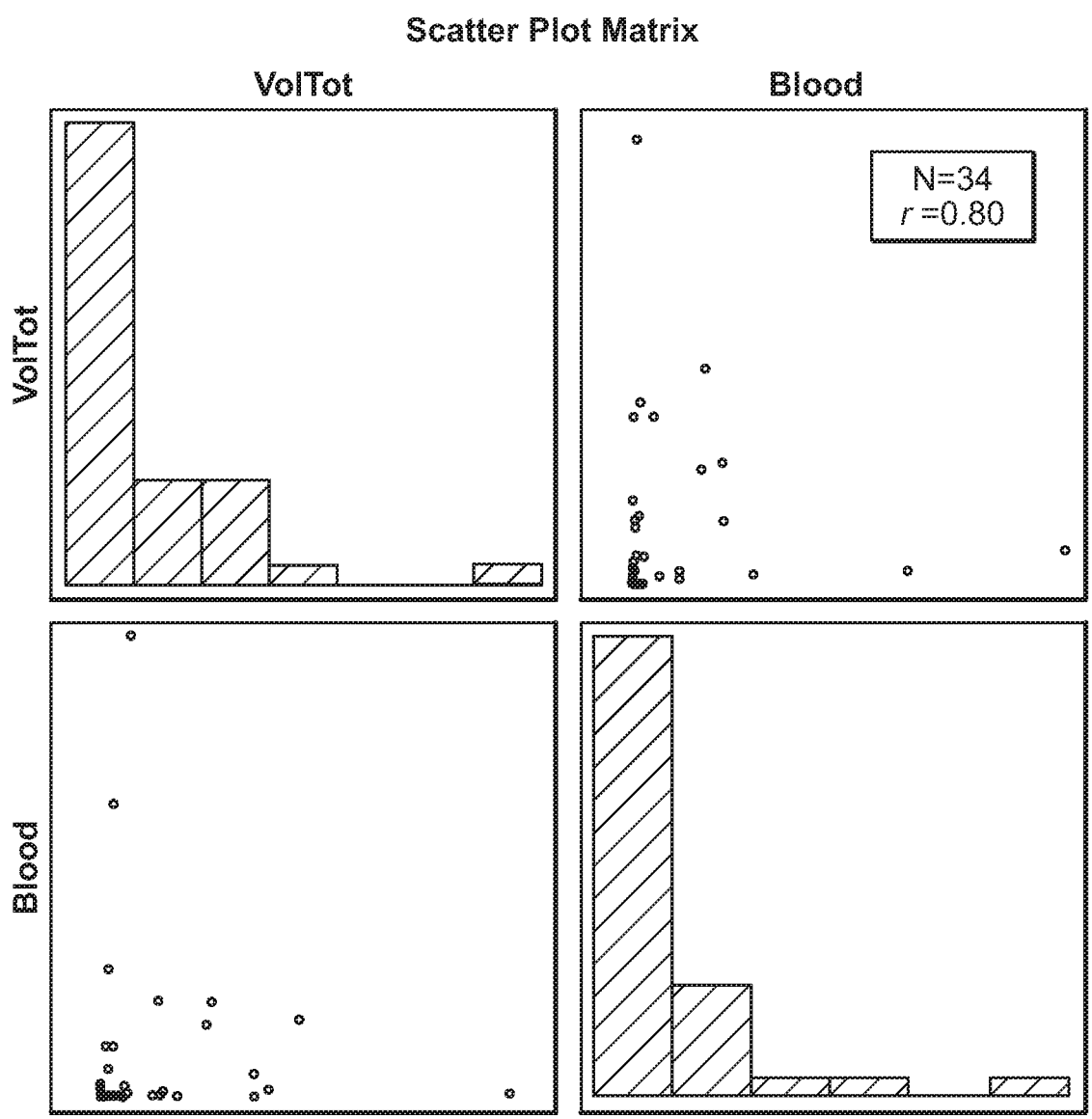
FIG. 9 depicts a scatter plot matrix showing that tumor volumes correlated with circulating tumor cell levels.

Using a 4.8 picogram threshold value for a "positive" serum test for BRAF$^{V600E}$, there is a high correlative with conventional cytological/pathological BRAF testing (FIG. 8). In addition, tumor volume correlates with circulating tumor cell levels (FIG. 9).

The results reported herein confirm the feasibility of a novel blood assay in detecting circulating mutant BRAF in the blood of patients with papillary thyroid carcinoma. This rapid assay has potential as a more cost-effective method for diagnosis, surveillance in thyroglobulin-antibody positive patients post-operatively, and in assessing evidence of disease over time in the adjuvant setting (i.e. treatment with BRAF-inhibitors).

The BRAF$^{V600E}$ mutation has been detected in patients with metastatic melanoma, colon, thyroid and other cancers. Recent studies suggested that tumors with this mutation are especially sensitive to BRAF inhibitors-hence the need to reliably determine the BRAF status of tumor specimens. The present technologies used to screen for this mutation fail to address the problems associated with infiltrating stromal and immune cells bearing wild type BRAF alleles and thus may fail to detect the presence of mutant BRAF$^{V600E}$ tumors. A rapid, inexpensive method was developed that reduces the contamination of wild type BRAF sequences from tumor biopsies. The protocol involves a series of PCR amplifications and restriction digestions that take advantage of unique features of both wild type and mutant BRAF RNA at position 600. Using this protocol, mutant BRAF can be detected in RNA from mixed populations with as few as 0.1% BRAF$^{V600E}$ mutant cells.

Figure 10:
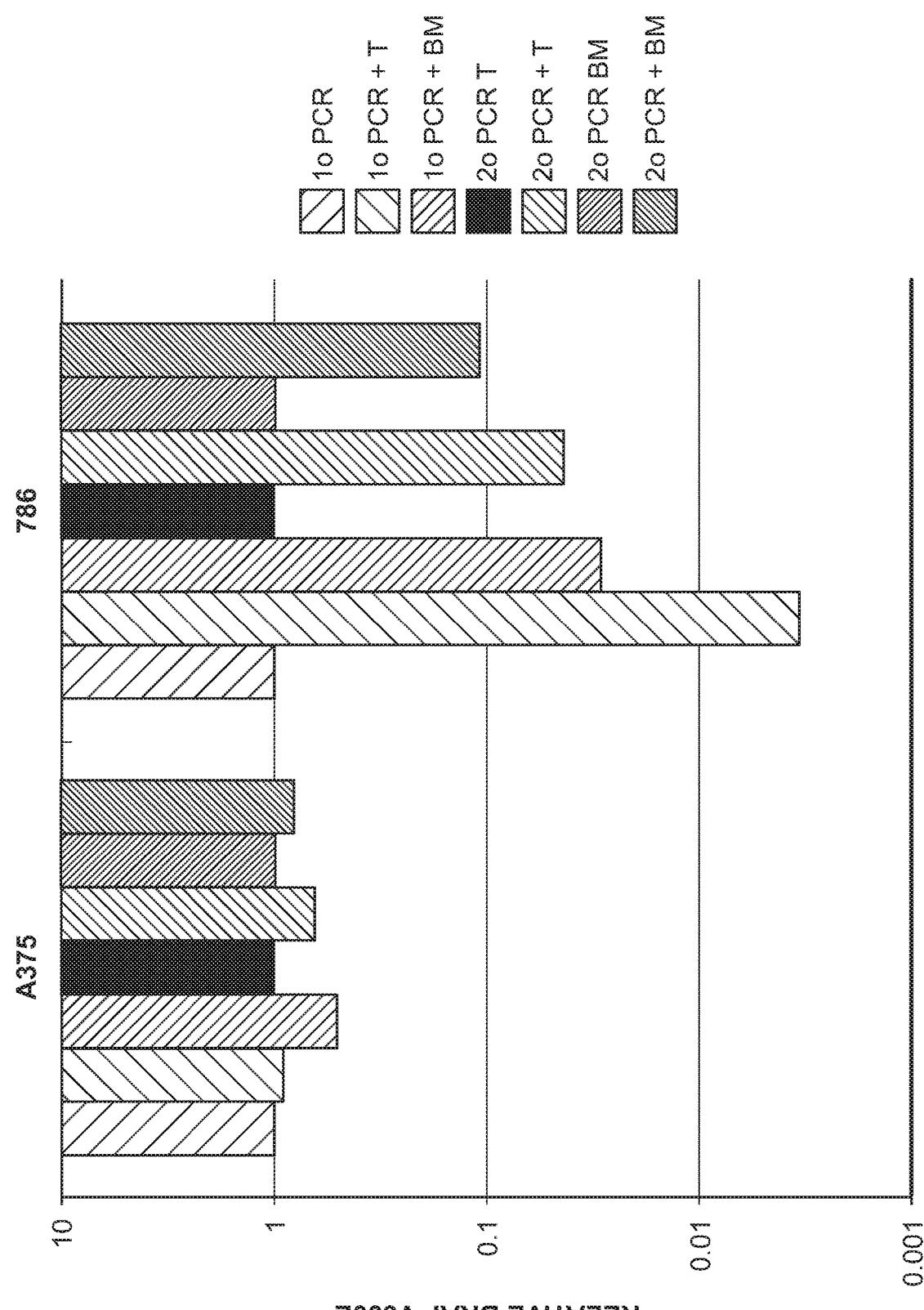
FIG. 10 depicts a bar graph showing increased efficiency of detecting $BRAF^{V600}$ with the BRAFV600E assay involving a series of PCR amplifications and restriction digestions using a homozygous $BRAF^{V600E}$ mutant cell line (A375) and a BRAF wild-type cell line (786-0). A TspR1 (or a different restriction enzyme with the same recognition sequence (BtslmutI (BM))) digestion after the initial or second PCR reduced contamination of wild type BRAF PCR product by preferentially digesting the wild type (TACAGT-GAA), but not the V600E mutated (TACAGAGAA) PCR product.
Figure 11:
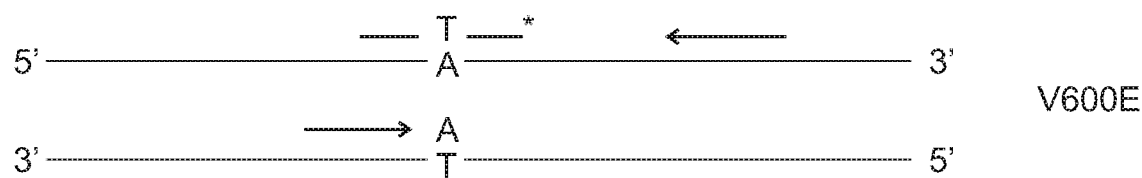
FIG. 11 is a schematic of the final real time PCR assay using a unique forward oligonucleotide and fluorescent probe with a single mismatch which are 100% matches for the mutant but not the wild type sequence.
Figure 11:
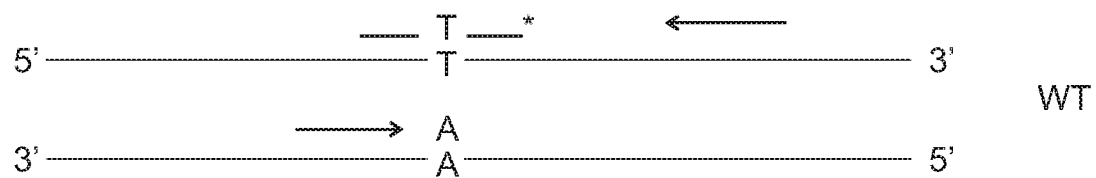
Figure 12A:
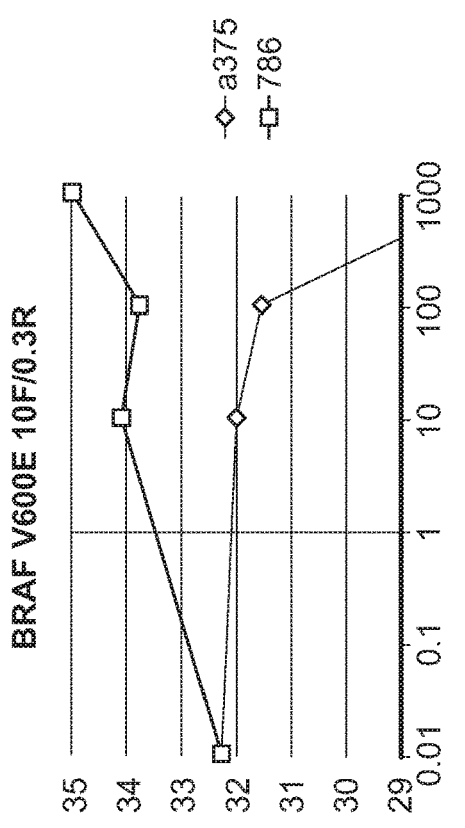
FIGS. 12A-12D provide four graphs showing that using a 33 fold excess of reverse oligo (R) over forward oligo (F) improved the specificity of the assay to detect $BRAF^{V600E}$.
Figure 12B:
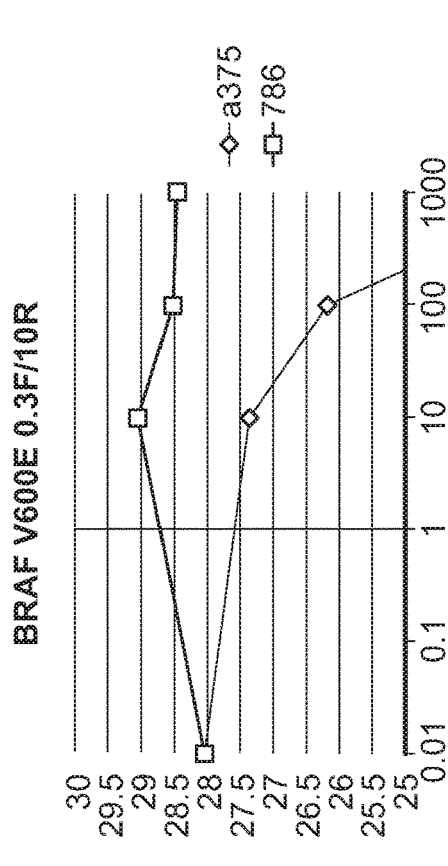
Figure 12C:
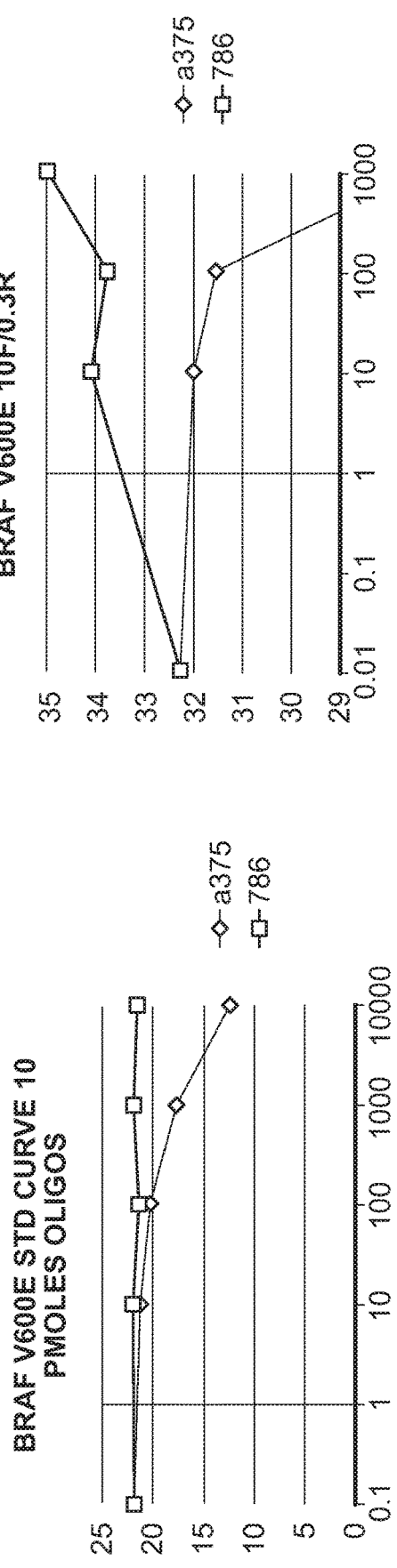
Figure 12D:
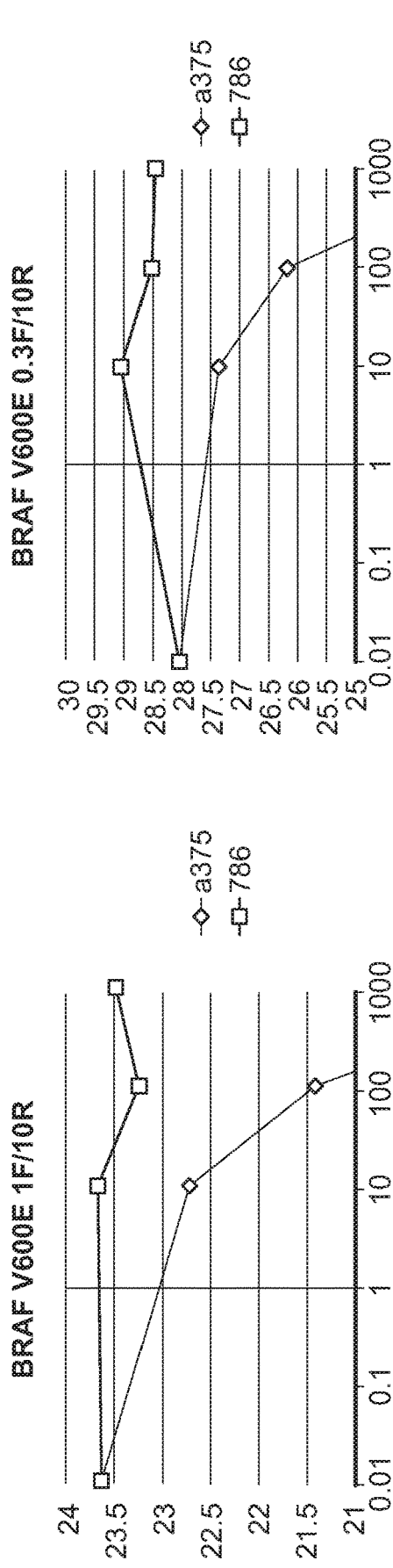

Example 3: An Assay Featuring a Restriction Enzyme Digestion Step Increased Specificity for BRAF$^{V600E}$ Detection An improved protocol for BRAF$^{V600E}$ level detection was developed including a TspR1 digestion after the initial PCR that reduced contamination of wild type BRAF PCR product in tissue and biopsy samples by preferentially digesting the wild type but not the V600E mutated PCR product (FIG. 10). In addition, in the final BRAF specific real time PCR the assay used a unique forward oligonucleotide and fluorescent probe with a single mismatch which were 100% matches for the mutant but not the wild type sequence (FIG. 11). Using a 33 fold excess of reverse oligo (R) to forward oligo (F) also improved the specificity for BRAF$^{V600E}$ detection (FIGS. 12A-12D).

Standard curves were generated using known amounts of purified primary PCR products of wild type and V600E BRAF as templates. The assay could reliably detect as low as 1 pg of BRAF$^{V600E}$ and exhibited a nearly 1000-fold difference in sensitivity for the V600E as compared to wild type BRAF PCR product (FIG. 5B).

To examine the specificity of the assay, the protocol was used in four cell lines: A375, a melanoma line with a homozygous BRAF$^{V600E}$ mutation, HT29, an adenocarcinoma line which is heterozygous for the BRAF$^{V600E}$ and 786-0 and Du145, renal cell carcinoma (RCC) and prostate cell lines, both wild type for BRAF. As shown in FIG. 5C, using equal amounts of input RNA (3 μg.), the A375 and HT29 cells expressed nearly 10,000 fold greater BRAF$^{V600E}$ than either wild type cell line. Using a cut-off value of 4.8 pg. in blood samples, the sensitivity of the assay for stage IV patients is 96% and the specificity 95%. The area under the receiver operator curve (ROC) was 0.9929, demonstrating an excellent ability to discriminate patients with and without BRAF-mutant melanoma (FIG. 5D).

Figure 13A:
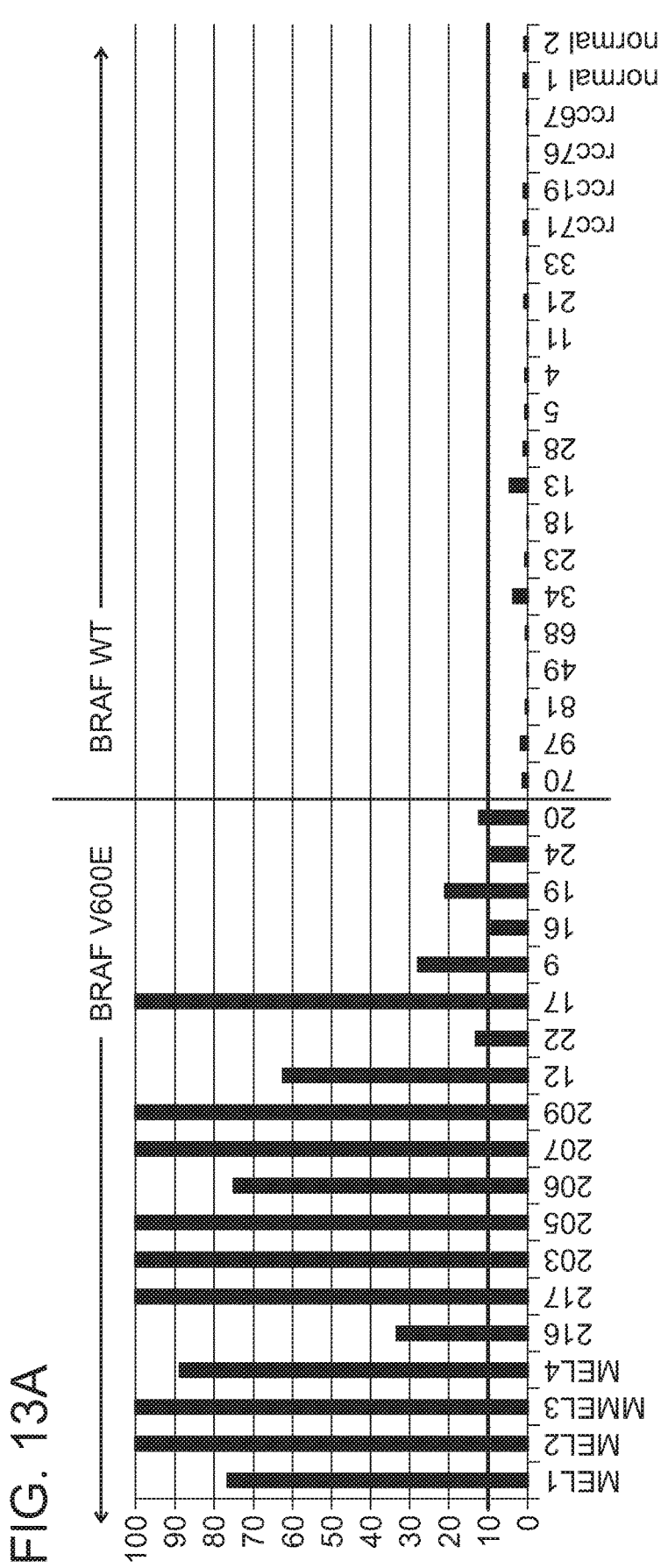
FIGS. 13A-13C are three graphs depicting distributions of BRAF levels by disease stage or mutation status. BRAF levels were transformed using natural logarithms (base e).
Figure 13B:
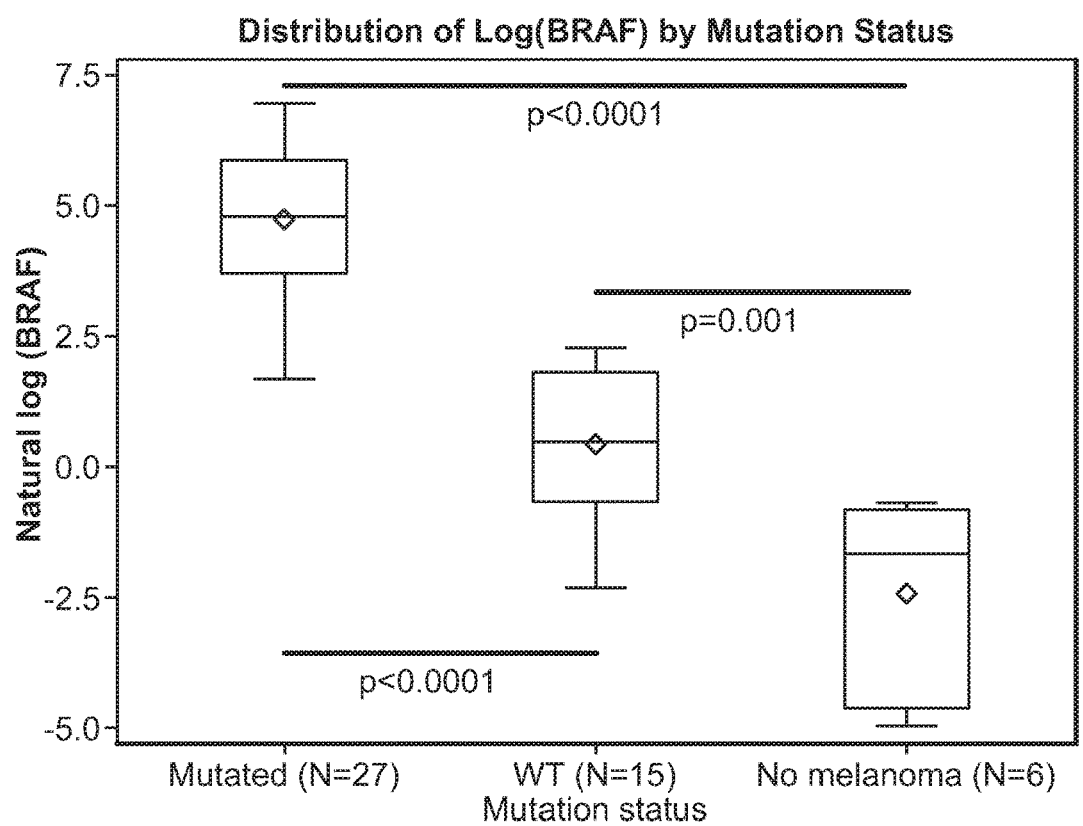
Figure 13C:
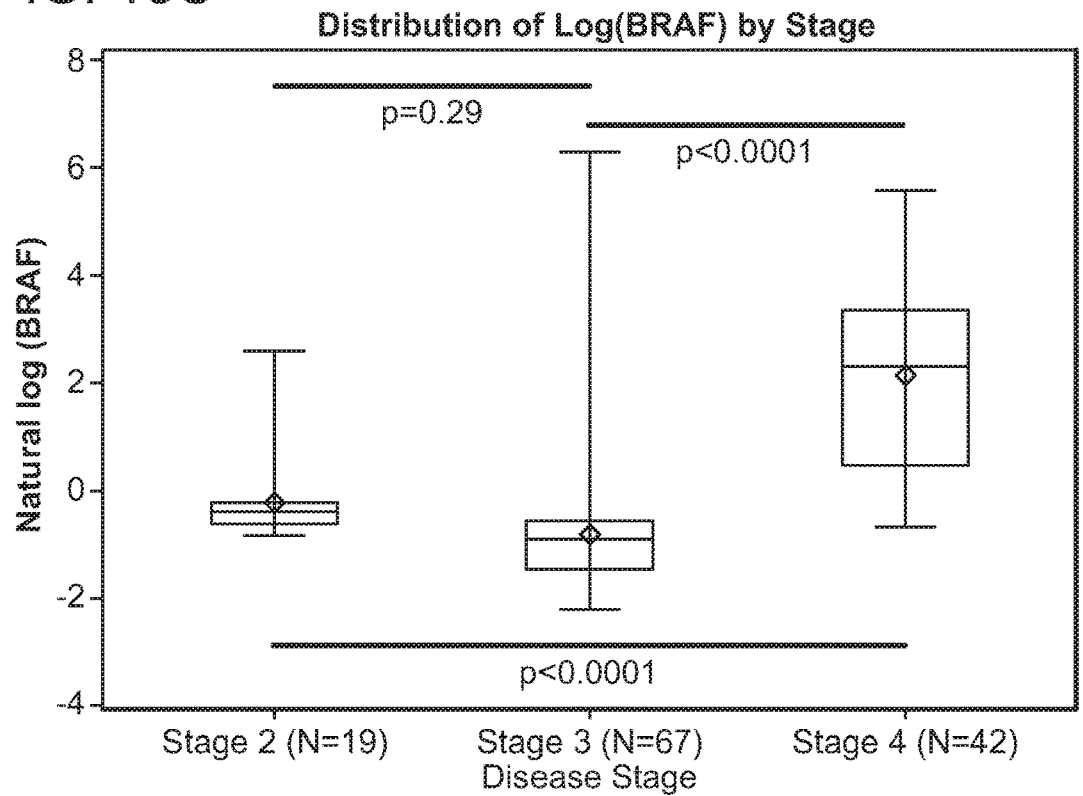

Example 4: BRAF$^{V600E}$ Blood Levels Differed Between Pre- and Post-Tumor Resection Samples obtained from 128 (42 Stage IV, 67 Stage III, and 19 Stage II) patients with melanoma were analyzed. A comparison of BRAF levels from 42 stage IV melanoma patients whose tumor biopsies had been previously determined to contain a V600E mutant (27 patients) or wild type BRAF (15 patients), 4 renal cell carcinoma (RCC) patients (known to be BRAF WT), and two normal controls was performed (FIGS. 13A and 13B). Mean BRAFV600 levels were 50.3 pg., 1.7 pg., and 1.2 pg. for patients with mutant disease, wild type melanoma, or RCC/non-melanoma, respectively (p<0.0001). In the 86 patients with Stage II and III melanoma, the median BRAF value from the post resection blood draws was 0.48 pg, regardless of the BRAF status by tissue analysis. A comparison of BRAF values in patients across stage II, III, and IV showed that patients with stage IV melanoma had significantly higher blood BRAF$^{V600E}$ values (FIG. 13C).

Figure 14A:
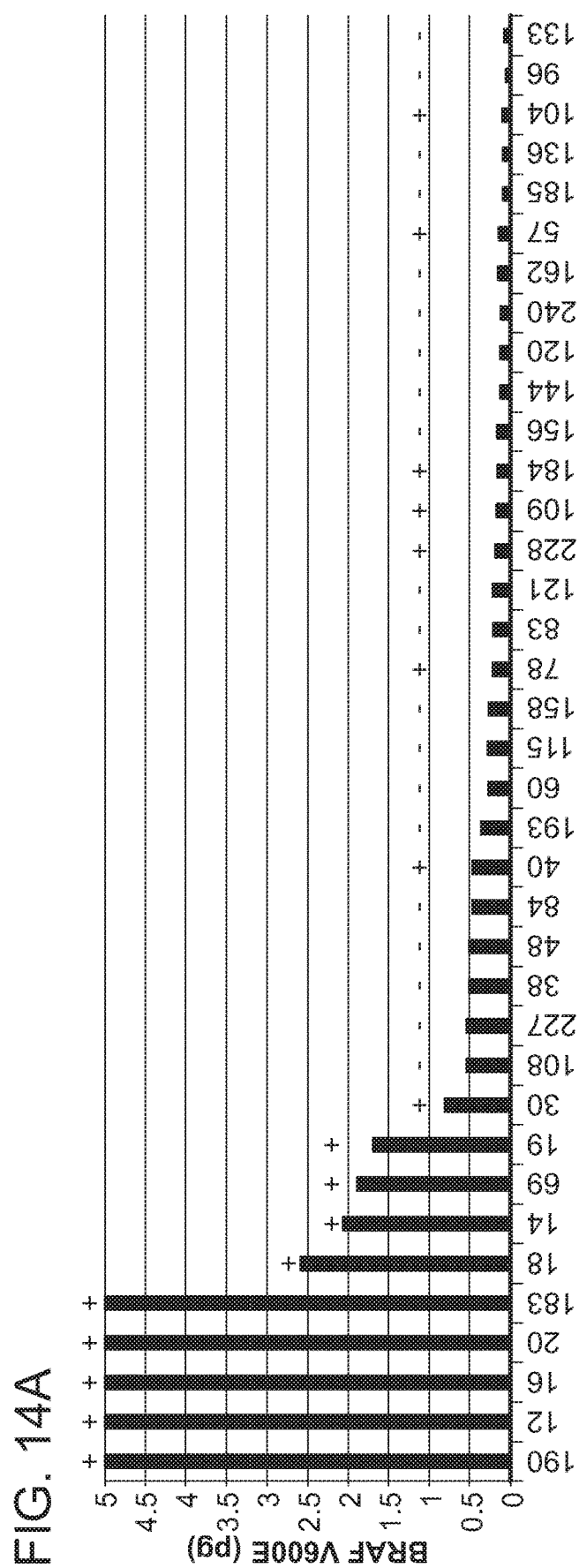
FIGS. 14A-14C depict two bar graphs showing BRAF V600E blood levels of Stage 2 and 3 melanoma cancer patients before and after surgical resection and a linear graph showing overall survival.
Figure 14B:
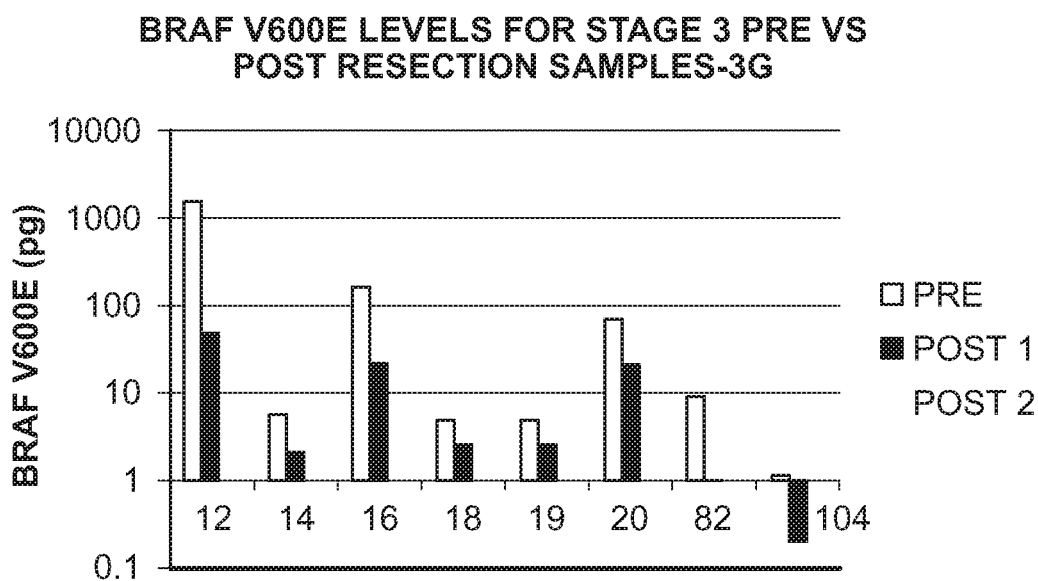

Thirty-seven of the 67 Stage III patients had tumor blocks suitable for tissue BRAF mutation analysis. In these patients, tissue-based analysis detected a BRAF$^{V600E}$ mutation in 17 patients. Using a cut-off value of 4.8 pg (determined from the Stage IV the receiver operator curve, ROC) in blood samples, 5 of the 17 patients with tissue BRAF detection had an elevated blood value. Further, the ten highest post-operative BRAF$^{V600E}$ levels in these patients were all patients with known BRAF mutations based on tissue analysis and none of the 20 patients without BRAF V600E detection in tissue had an elevated V600E value (FIG. 14A). Of note, the mean BRAF value in the 17 patients with known BRAF mutation in tissue was 21 pg compared with 0.26 pg in the 20 patients without identified mutation in tissue, though this difference did not meet statistical significance (p<0.128). In order to address the high number of post resection blood samples that had negative BRAF$^{V600E}$ levels despite being tissue positive, pre- vs. post-resection samples were compared. All samples were previously determined to be BRAF$^{V600E}$ by tissue analysis. As shown in FIG. 14B, all 8 patients showed a marked decreased in BRAF$^{V600}$ levels post surgery.

Figure 14C:
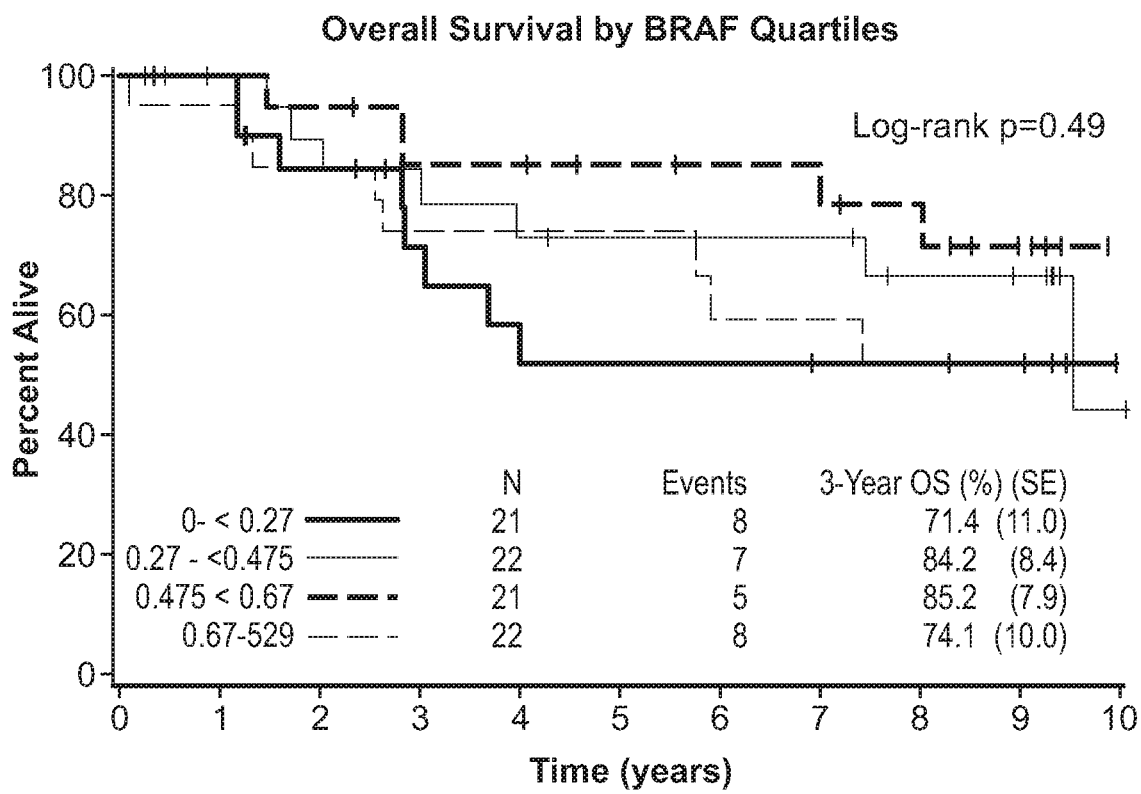

Furthermore five patients had post-operative levels below the level of detection (4.8 pg) for this assay. The reduced tissue burden as a result of surgical resection provided a plausible explanation for the approximate 70% discordance between tissue and post surgical blood analysis by this assay. Additionally, comparisons in all 86 stage 2 and 3 patients of blood BRAF values post surgery were made according to stage (Stage II vs. Stage III), sub-stage (Stages II and III A, B, and C), and intermediate versus high risk, defined as risk of death <50% (AJCC Stage IIA, IIB, or IIIA) or >50% (Stage IIC, IIIB, IIIC), and showed no significant differences. In the 86 patients with resected, stage II or III melanoma, 39 had evidence of disease relapse (45.3%). In all these patients, detectable oncogenic BRAF mutation in the blood was not associated with a difference in the risk of relapse (5-year RFS: 52% vs. 57%, logrank p=0.98) or death (5-year OS: 73% vs. 75%, log-rank p=0.88). Analysis of BRAF levels quartiles similarly showed no evidence of OS difference (FIG. 14C). These findings show that this assay can detect the BRAF$^{V600E}$ mutation in resected stage II and III patients, regardless of the tumor BRAF status.

Figure 15A:
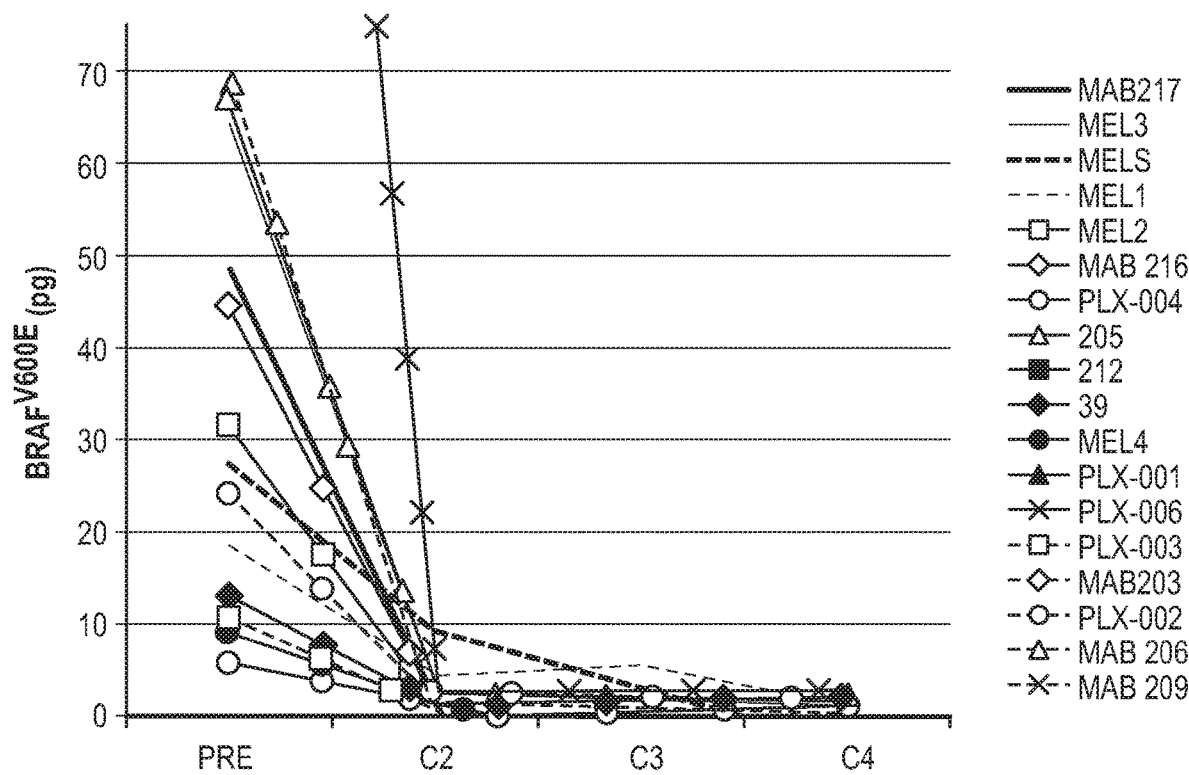
FIGS. 15A and 15B provide two graphs that show that blood $BRAF^{V600E}$ levels in 18 patients with $BRAF^{V600E}$ melanoma treated with either vemurafenib (12 patients) or the combination of dabrafenib and trametinib (6 patients) dramatically reduced following the commencement of therapy.
Figure 15B:
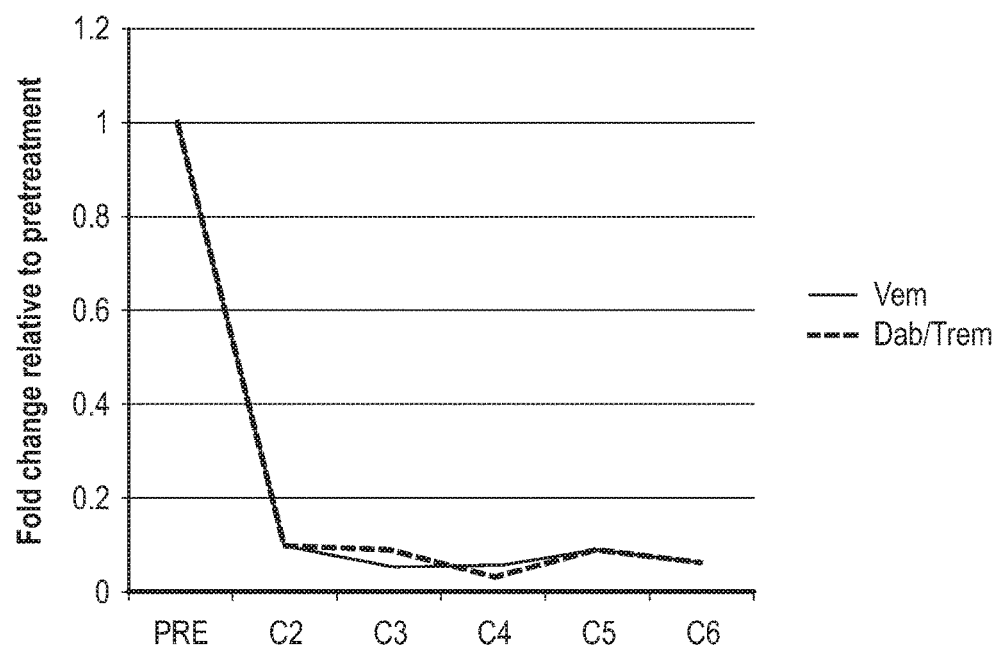
Figure 16A:
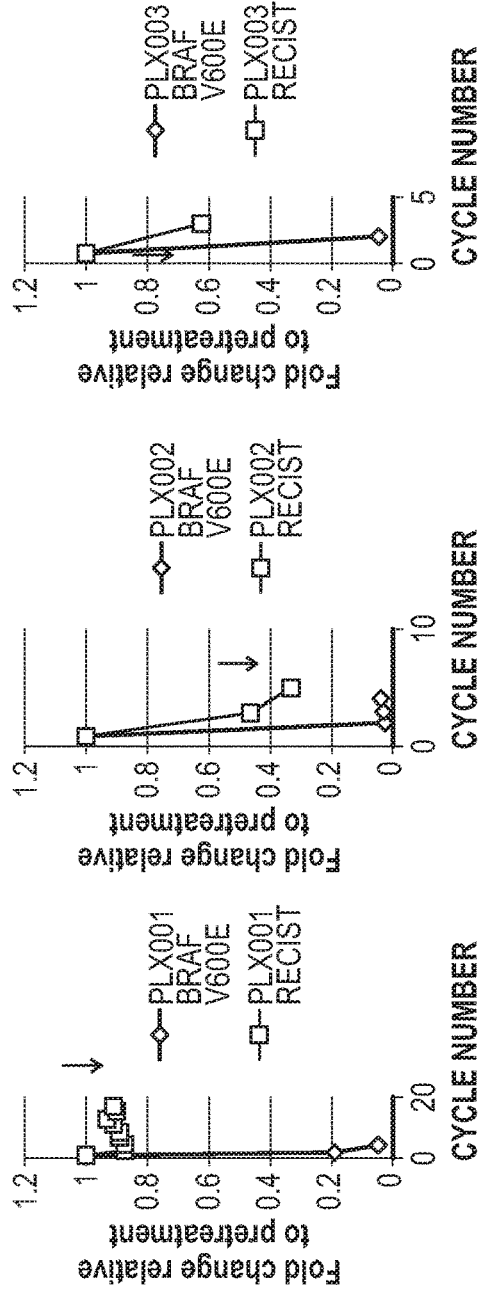
FIGS. 16A-16C show three groups of graphs of serial blood BRAF V600E levels (pg) compared to tumor volume by RECIST (Response Evaluation Criteria In Solid Tumors) from 11 patient treated with the BRAF inhibitor vemurafenib and 6 patients treated with the BRAF inhibitors dabrafenib and trametinib until removed from the study due to progressive disease (the time of disease progression is shown with an arrow).
Figure 16A:
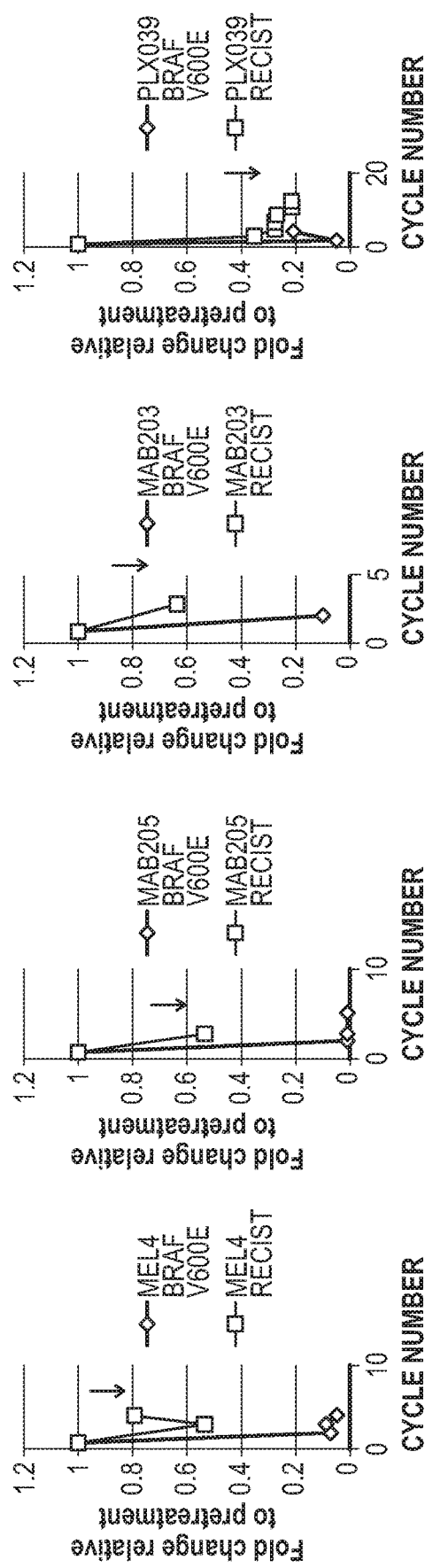
Figure 16B:
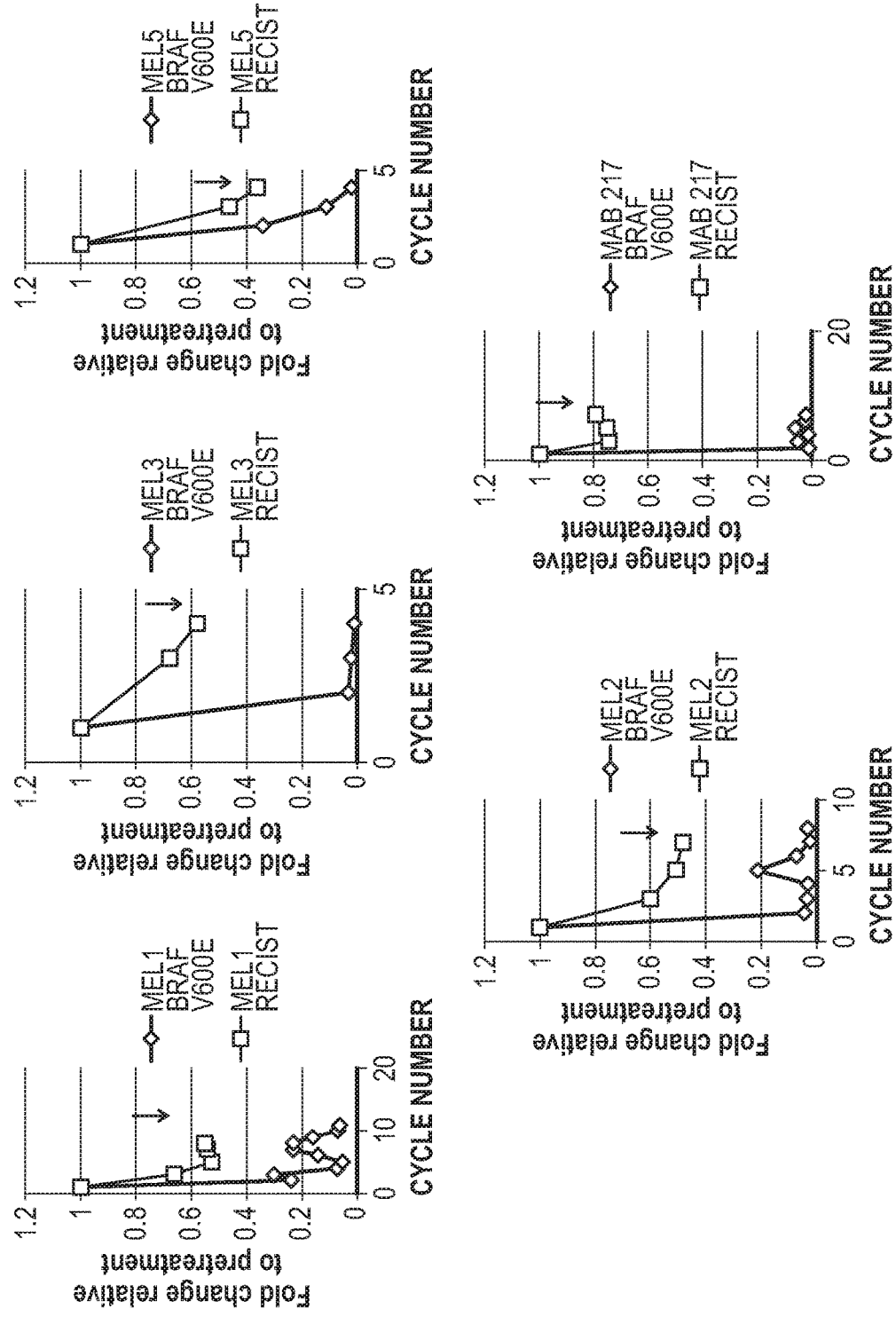
Figure 16C:
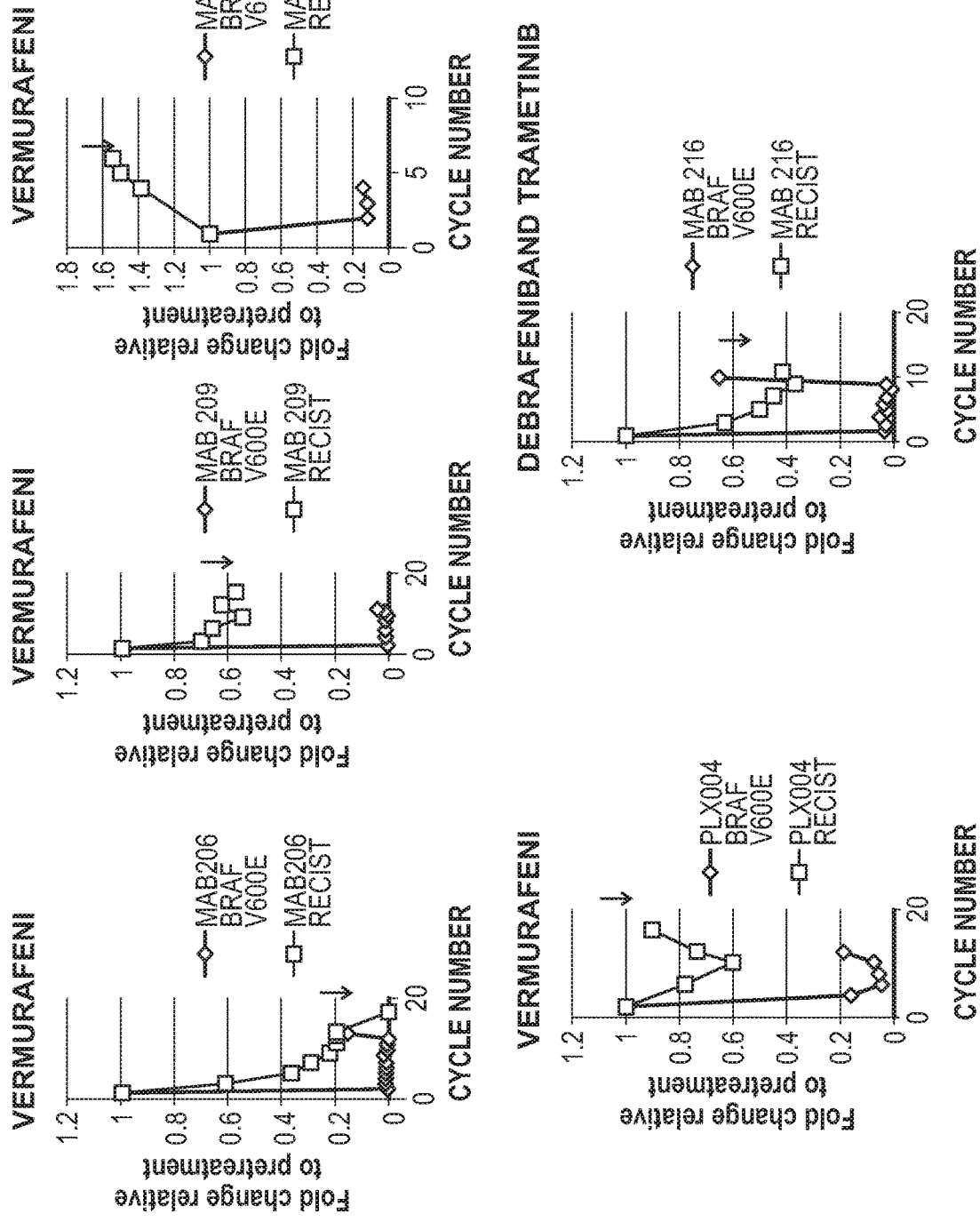

Example 5: BRAF$^{V600E}$ Blood Levels Decreased Post Treatment with BRAF Inhibitors Blood BRAF$^{V600E}$ levels in 18 patients with BRAF$^{V600E}$ melanoma treated with either vemurafenib (12 patients) or the combination of dabrafenib and trametinib (6 patients) were dramatically reduced following the commencement of therapy (FIGS. 15A and 15B), and this reduction was similar in patients treated with single-agent BRAF or combination BRAF-MEK inhibitor therapy. FIGS. 16A-16C shows the serial values of the BRAF$^{V600E}$ level in the blood of eleven patients treated with single agent vemurafenib and all six patients treated with dabrafenib and trametinib in whom tumor measurements from serial CAT scans acquired by patients until disease progression were also plotted alongside the blood BRAF$^{V600E}$ data. In the majority (15/17) of patients a reduction in blood BRAF$^{V600E}$ level correlated with disease response on imaging. After the decrease in BRAF$^{V600E}$, five of the seventeen patients showed an increase in BRAF$^{V600E}$ in the blood 42-112 days prior to having treatment stopped due to disease progression (FIG. 16C). Of note in all 17 patients treatment was halted due to the occurrence of new lesions or non-target lesion progression and not due to target lesions progression.

Blood-based detection of oncogenic mutations has become increasingly widespread. Alternative methods make use of real time PCR, mass spectrometry, allelic specific PCR, PCR using locked oligonucleotides to suppress wild type sequences, direct sequencing of RNA or DNA to preferentially distinguish the mutant V600E from wild type BRAF, as well as a combination of emulsion-based digital PCR and flow cytometry (so-called Beads, Emulsion, Amplification, and Magnetics or BEAMing). The present assay was unique due to the approach that lead to its high sensitivity and specificity. This was achieved by both, the use of RNA from peripheral blood lymphocytes (PBLs) isolated from Ficoll, as it was postulated these cells contained either circulating tumor cells (CTCs) or other encapsulated, circulating RNA-containing factors released by tumors, and the reduction of background from wild type BRAF with the use of TspR1, a restriction enzyme that preferentially digests only the wild type sequence from the first PCR product. (Panka et al., 2010, Melanoma research 20:401-7.; Fusi et al., 2011, Eur J Cancer; 47:1971-6.) As a result, a highly sensitive assay (96% in patients with active, metastatic disease) was developed that had exquisite specificity (95% in these same patients) and was able to provide quantitative information due to the use of V600E-specific Real-Time PCR.

An initial application of this assay would be to diagnose BRAF-mutant disease. Current tissue-based BRAF mutational methods can be challenging in archived primary melanomas (tumor heterogeneity) and microscopic nodal metastases (lack of sensitivity), and patients with newly metastatic melanoma often have rapidly progressive disease that requires urgent identification of mutational analysis. Analyzing blood for the BRAF mutation would prove to be a more efficient and possibly more reliable method of determining a patient's BRAF status. The sensitivity and specificity seen with the present assay was encouraging.

A second use of this assay would be in the Stage II and III setting, as the optimal follow up of patients who were rendered disease-free with surgery for their melanoma was unknown. The development and validation of a blood-based prognostic biomarker would offer the potential to improve the National Comprehensive Cancer Network (NCCN) guidelines and direct radiographic imaging. The present data showed that while blood BRAF$^{V600E}$ levels reduced following surgery, post-operative blood-based analysis might be useful in diagnosing BRAF$^{V600E}$ status. Proof-of-concept was demonstrated that blood BRAFV600E levels could be detected in the blood of patients with resected melanoma. It is conceivable that the BRAF level would change over time and that this change in level over time might be more predictive of outcome than a one-time value. Investigation into this specific application of this assay is underway (NCT01840527).

Finally, an assay that has the potential to identify tumor resistance to BRAF-directed therapy at an earlier time point is desperately needed. BRAF inhibitor resistance typically develops within 6-8 months following initial tumor regression, but with a range of 2 months to 2 years. Importantly, each described mechanism involved the retention of the initiating BRAF mutation. As the mechanisms of resistance are now being elucidated, diagnostic assays, which may identify emerging resistance at an earlier time-point than standard clinical or radiographic assessments, would enable more prompt switching to another therapy. This was particularly important due to the fact that a number of patients treated with BRAF inhibitors progressed quite quickly following initial disease regression. More advanced notice of disease progression, when disease growth is more modest, would allow for a more timely change in treatment and improved benefit of next line therapy. To date, only a small number of patients have been followed serially (17 presented here) with the present assay in the context of BRAF-directed therapy. Still, this was the largest number presented to date followed with serial testing with a quantitative BRAF assay. These findings—that BRAF level reduced with the initiation of BRAF inhibitor therapy and typically increased at the time of or in advance of radiographically-defined disease progression—are compelling. They also serve as a proof of concept that this type of assay might have value in this patient population and treatment setting.

In conclusion, the clinical utility of the first blood-based, BRAF detection and quantification assay in a number of clinical settings was reported. The present data provided proof of concept that circulating blood-BRAF could be collected, quantified, flowed, and utilized in patients with Stage II, III, and IV melanoma.

The results reported herein above were carried out using the following methods and materials.

Melanoma Analysis

The melanoma cell lines A375, A2058 and SK MEL 5, kidney cancer cell line 786-0, colon adenocarcinomas HT29 and DLD-1, prostate carcinoma DU145, and the breast carcinoma MCF7 were purchased from ATCC (Manassas, Va.). Tumor samples and peripheral blood lymphocytes were obtained from patients with advanced melanoma as part of an IRB approved tissue banking protocol (DFHCC 02-017). Peripheral blood lymphocytes (PBLs) were isolated by Ficoll density centrifugation (Wilson et al., 1975, J Immunol Methods; 9:67-8.). Oligonucleotides were custom synthesized from Invitrogen (Carlsbad, Calif.).

RNA from Ficoll purified peripheral blood lymphocytes (PBLs) or cell lines was isolated by the trizol method (Invitrogen) and (3 pg) reverse transcribed to cDNA by standard methods using M-MLV reverse transcriptase (Invitrogen) and oligo (dt)15 (Promega; Ju et al., 1995, Nature; 373:444-8). The cDNA was subjected to real time PCR for 18S RNA in order to normalize the quantity, as well as quality of the input RNA prior to the next step (ABI for oligo/probe set). The equilibrated cDNA was PCR amplified using PCR master mix (Promega) and oligonucleotides [5'(CCATATCATTGAGACCAAATTTGAGATG)3' and 5'(GGCACTCTGCCATTAATCTCTTCATGG)3'] that produced a product of 466 bp including the mutation site at position 600. The PCR conditions were 94° for 2 minutes followed by 40 cycles of 94° for 1 minute, 60° for 2 minutes and 72° for 2 minutes with a final incubation of 72° for 7 minutes. After cleanup using a purification column, NucleoSpin® extract column (Clontech), a portion of the PCR product was digested with TSPR1 (restriction site=NNCASTGNN, New England Biolabs, Beverly, Mass., USA) at 65° for 16 hours. Only wild-type BRAF and not V600E mutant BRAF PCR product was digested by this enzyme. This digestion was added to reduce the amount of contaminating normal BRAF from surrounding and infiltrating normal tissue in the blood samples. A 1/100 dilution of the TSPR1 digested material was then PCR amplified a second time using nested oligonucleotides 5'(ACGC-CAAGTCAATCATCCACAGAG)3' and 5'(CCGTACCT-TACTGAGATCTGGAGACAGG)3' producing a product of 331 bp, which was enriched in PCR products containing the position 600 mutation. The conditions of the PCR were the same as the first PCR except the amplification was 45 cycles for peripheral blood lymphocytes (PBLs) instead of 40 cycles. After a second cleanup using a NucleoSpin extract column, the DNA (1/1000 dilution) was digested again with TspR1 and then subjected to a BRAF$^{V600E}$ real time PCR as described (Fusi et al., 2011, Eur J Cancer; 47:1971-6.). The annealing and extension temperature was adjusted to 64° resulting in a more favorable amplification of the mutant as compared to the wild type templates (FIG. 5B) than was reported (Fusi et al., 2011, Eur J Cancer; 47:1971-6.). To further favor the mutant over the wild type product, a 33-fold excess of the reverse (common sequence in mutant and wild type) to forward (exact match for mutant and 1 base mismatch for wild type sequences) primers were used in the real time PCR assay. Therefore, after two rounds of TspR1 digestion it is highly unlikely that any remaining wild type product would have a significant impact on the assay. Purified BRAF$^{V600E}$ first round PCR product with a known concentration was also run through the assay and was used to create a standard curve. Using the standard curve the amount of end product was determined.

Thyroid Cancer

Cell Lines, Tissue Acquisition and Oligonucleotides

The melanoma cell line A375, kidney cancer cell line 786-0, colon adenocarcinoma HT29 and prostate carcinoma DU145 were purchased in 2013 from ATCC (Manassas, Va., USA). All four cell lines were authenticated by isoenzymology and the Cytochrome C subunit I (COI) PCR assay was performed for confirmation of species. In addition, the cell lines had their identity confirmed by STR analyses. Oligonucleotides were custom synthesized from Invitrogen (Carlsbad, Calif., USA) and Sigma (St Louis, Mo.). Tumor samples and peripheral blood lymphocytes were obtained from patients with thyroid cancer and processed as for melanoma.

The Protocol in Brief

Figure 5A:
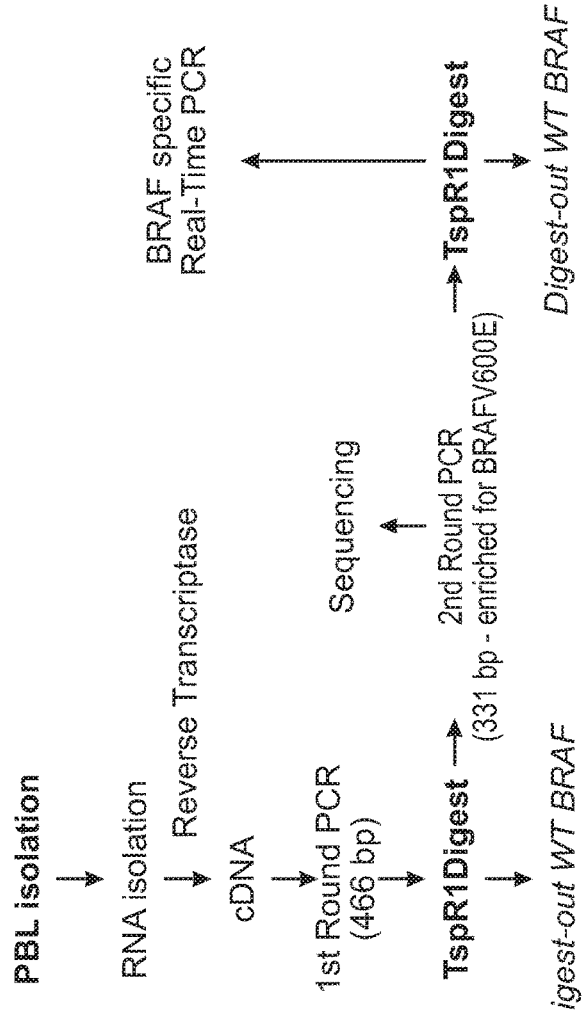
FIGS. 5A-5D provide a schematic of the BRAFV600E assay, a standard curve, a bar graph showing results of BRAFV600E analysis and a graph of a receiver operator curve (ROC).
Figure 5C:
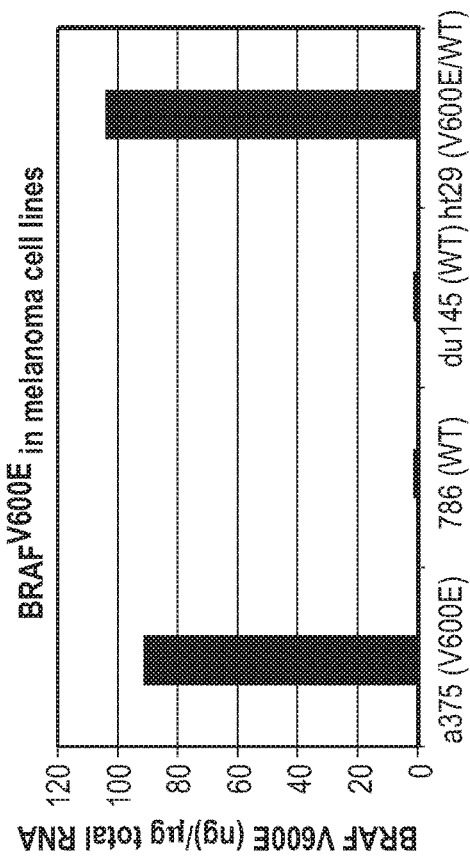
Figure 5B:
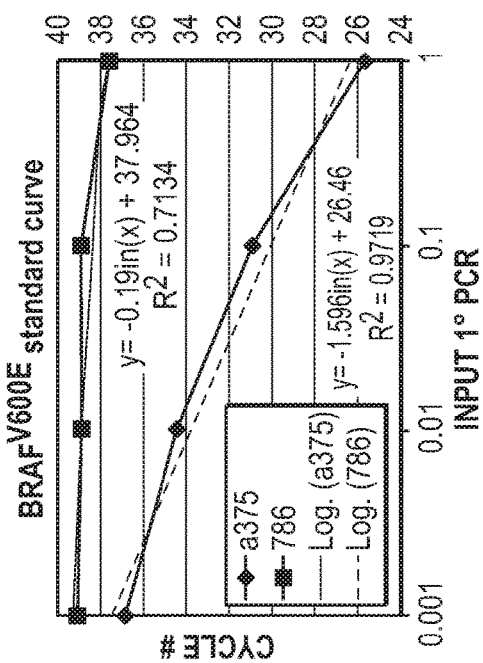
Figure 5D:
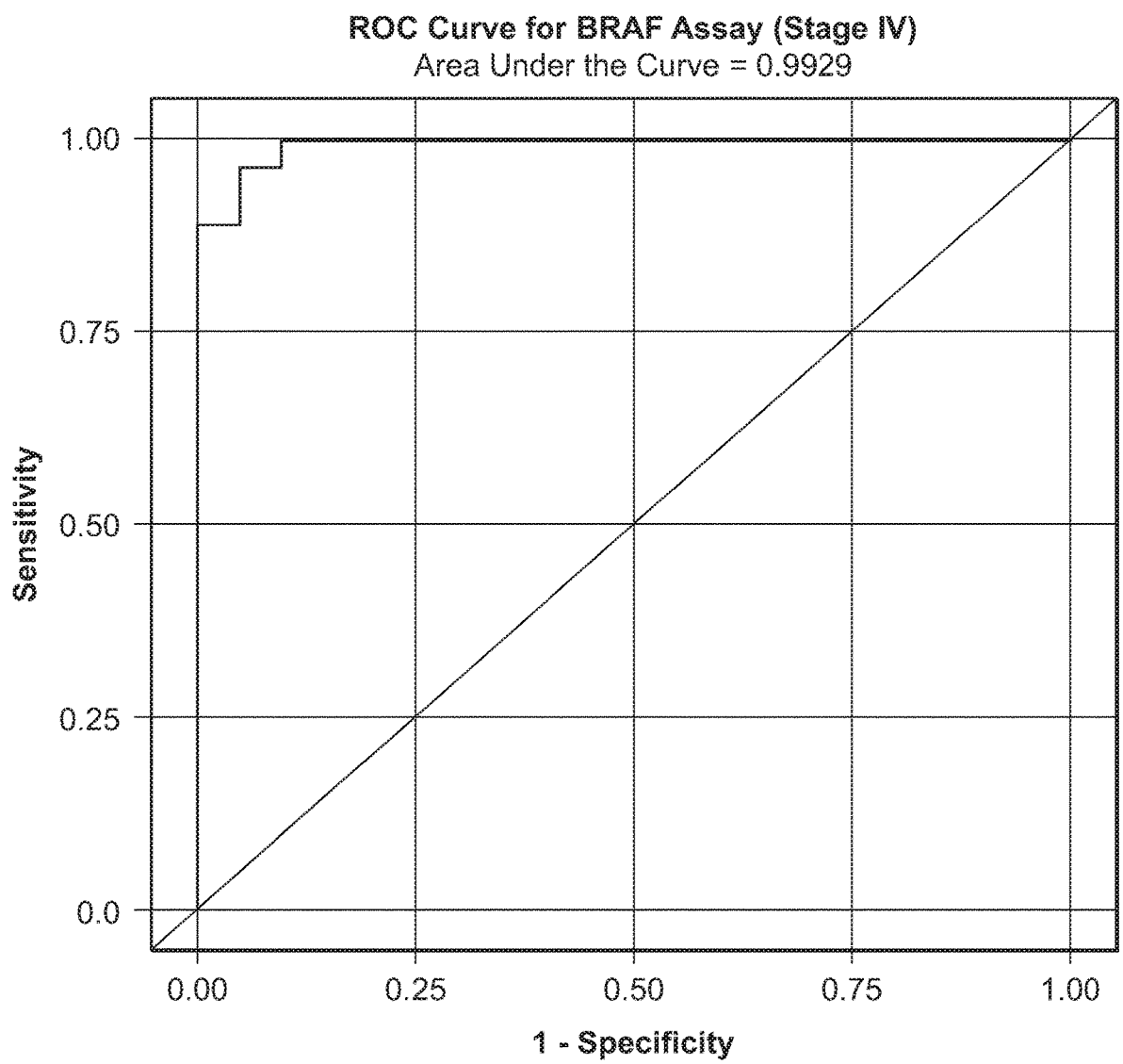

As illustrated in FIG. 5A, an initial RT-PCR is followed by digestion with TspR1 (restriction site=NNCASTGNN), which preferentially digests the wild-type (TACAGTGAA) product but not the V600E mutated (TACAGAGAA) PCR product. In addition, none of the other less frequently reported V600 mutations (V600D, V600M, V600G, V600A, V600R, V600K, or V600G) are substrates for TspR1. A second, nested PCR using the digested material follows. After a second digestion with TspR1, the product is subjected to a real time PCR specific for the V600E mutation and not wild type sequences.

Peripheral Blood Isolation

Figure 17:
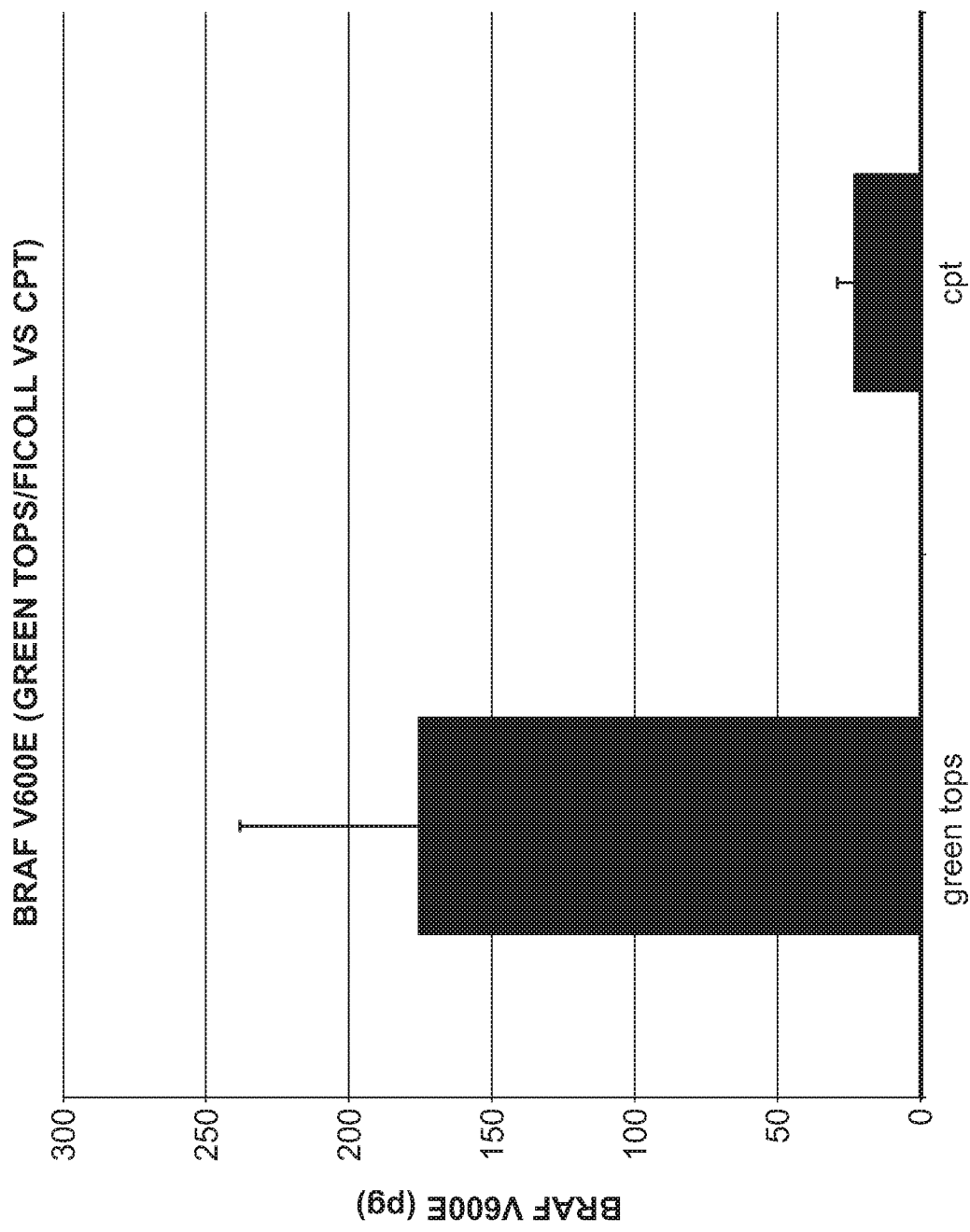
FIG. 17 is a bar graph showing BRAF V600E levels in patients with detectable $BRAF^{V600E}$ mutation in tissue who had peripheral blood cell isolation using Cell Preparation Tubes (CPT) tubes versus Ficoll (p<0.056).

Peripheral blood lymphocytes (PBLs) were obtained from 128 patients with advanced or cutaneous melanoma as part of IRB approved tissue-banking protocols (DFHCC 02-017 and 11-181). Peripheral blood lymphocytes (PBLs) were isolated by Ficoll density centrifugation (Wilson et al., 1975, J Immunol Methods; 9:67-8.). Of these 128 patients, 42 had stage IV disease and had blood collected specifically for this analysis between 2009 and 2012. Peripheral blood lymphocytes (PBL) from the 19 patients with stage II melanoma and 67 patients with stage III disease were collected and isolated approximately 4-8 weeks following completion of surgical management as part of the Harvard Skin SPORE between 2002 and 2006. These samples were stored in freezing medium (95% fetal calf serum with 5% DMSO) at −80 degrees Celsius (stage IV samples) or in liquid nitrogen (stage II and III samples). Furthermore, blood was drawn pre- and post-resection from 8 stage III patients previously determined to be BRAFV600E by tissue analysis. Only one sample per patient was available for most patients involved in this study and in all of the patients with Stage II or III disease (except for the aforementioned 8 patients with stage III disease with pre- and post-operative samples). Serial blood samples were collected and assayed from twelve patients receiving the BRAF inhibitor vemurafenib and six patients receiving the combination of dabrafenib and trametinib. Samples were collected until RECIST (Response Evaluation Criteria In Solid Tumors)-determined disease progression was documented in 17 of these 18 patients. In a subset of patients, different tubes were utilized after initiation of BRAF-directed therapy. Specifically, Cell Preparation Tubes (CPT) were utilized and the cellular component was removed and analyzed. Analyses comparing the two techniques (Ficoll isolation and CPT tube isolation) revealed a 7.5-fold greater BRAF level when Ficoll was used compared with CPT tube isolation (FIG. 17). As a result, only samples isolated using Ficoll isolation were analyzed in this study.

Tissue-Based BRAF Analysis

Patients with stage IV melanoma had BRAF mutational analysis on tumor tissue as part of standard of care either via the Cobas assay (Clarient Labs) or via SNaPshot (Massachusetts General Hospital Cancer Center Translational Research Laboratory; Halait et al., 2012, Diagnostic molecular pathology: the American journal of surgical pathology, part B; 21:1-8; Su et al., 2011, The Journal of molecular diagnostics: JMD; 13:74-84).

Statistical Analysis

Summaries of BRAF expression levels over time are presented using descriptive methods. Comparisons of BRAF expression according to mutational status or stage of disease were based linear regression models of natural log(BRAF) with mutational status or stage as the single predictor. Bonferroni corrections were used for pairwise comparisons to adjust for multiplicity. The distributions of relapse-free survival (RFS) and overall survival (OS) are described using the method of Kaplan-Meier. Five-year estimates of RFS and OS are presented with 95% confidence intervals calculated using log(−log(RFS or OS)) methodology. Statistical significance is defined as $p<0.05$; there are no adjustments for multiple comparisons.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method for detecting a BRAF$^{V600E}$ mutation in a biological sample, the method comprising
providing a cDNA that is reverse transcribed from RNA isolated from a biological sample of a subject;
amplifying the cDNA with a forward oligonucleotide to obtain a BRAF amplicon, wherein the forward oligonucleotide comprises an exact match to a nucleic acid encoding amino acid residue 600 in a BRAF mutant protein and is a single base mismatch to a nucleic acid encoding amino acid residue 600 in a wild-type BRAF protein;
digesting the BRAF amplicon with a TspR1 restriction enzyme; and
detecting a level of the BRAF amplicon with a probe, wherein the probe comprises an exact match to a nucleic acid encoding amino acid residue 600 in the BRAF mutant protein and is a single base mismatch to a nucleic acid encoding an amino acid residue 600 in a wild-type BRAF protein, and wherein a level greater than about 5 pg of the BRAF amplicon indicates the presence of a BRAF$^{V600E}$ mutation in the biological sample.

2. The method of claim 1, wherein the biological sample comprises a mixed population of cells.

3. The method of claim 2, wherein the mixed population of cells comprises an infiltrating stromal and/or immune cell comprising a wild-type BRAF allele.

4. The method of claim 2, wherein the method detects the BRAF$^{V600E}$ mutation from about 0.1% BRAF$^{V600E}$ mutant cells.

5. The method of claim 1, wherein a level of BRAF$^{V600E}$ is greater than about 20, 30, 40, 50 or 100 pg.

6. The method of claim 1, wherein the cDNA is amplified using real time PCR.

7. The method of claim 1, further comprising comparing the level of the BRAF amplicon detected to a standard curve obtained using a known concentration of cDNA.

8. A method of treating thyroid cancer or melanoma in a pre-selected subject, the method comprising administering an effective amount of an agent to the pre-selected subject, wherein the agent is selected from the group consisting of vemurafenib, dabrafenib, trametinib, and ipilimumab, or combinations thereof, and wherein the subject is pre-selected by detecting a level of a BRAF$^{V600E}$ mutation according to the method of claim 1 in a biological sample isolated from the subject.

9. The method of claim 8, wherein the subject has a thyroid cancer or melanoma that has acquired resistance to a treatment regimen and/or relapsed.

10. The method of claim 8, wherein a level of BRAF$^{V600E}$ greater than 10 pg in the sample pre-selects the subject for treatment.

11. The method of claim 8, further comprising measuring the level of BRAF$^{V600E}$ in the biological sample isolated from the pre-selected subject prior to treatment relative to a level of BRAF$^{V600E}$ present in a second biological sample isolated from the pre-selected subject after treatment, wherein an increase in the level of BRAF$^{V600E}$ is indicative that the thyroid cancer or melanoma has developed resistance and/or has relapsed, and a decrease indicates that the treatment is effective.

12. The method of claim 8, wherein the biological sample is a blood sample, a biopsy or a needle biopsy.

13. The method of claim 12, wherein the blood sample comprises peripheral blood lymphocytes.

14. A method for detecting a BRAF$^{V600E}$ mutation in a biological sample, the method comprising
(a) amplifying a cDNA to obtain a first BRAF amplicon, wherein the cDNA is reverse transcribed from RNA isolated from a biological sample of a subject;
(b) digesting the first BRAF amplicon with a TspR1 restriction enzyme to obtain a first digested material;
(c) amplifying the first digested material to obtain a second BRAF amplicon;
(d) digesting the second BRAF amplicon with the TspR1 restriction enzyme to obtain a second digested material;
(e) amplifying the second digested material with a forward oligonucleotide to obtain a third BRAF amplicon, wherein the forward oligonucleotide comprises an exact match to a nucleic acid encoding amino acid residue 600 in a BRAF mutant protein and is a single base mismatch to a nucleic acid encoding amino acid residue 600 in a wild-type BRAF protein; and
(f) detecting the third BRAF amplicon with a probe, wherein the probe comprises an exact match to a nucleic acid encoding amino acid residue 600 in the BRAF mutant protein and is a single base mismatch to a nucleic acid encoding amino acid residue 600 in the wild-type BRAF protein,
wherein a level greater than about 5 pg of the third BRAF amplicon detected indicates the presence of a BRAF$^{V600E}$ mutation in the biological sample.

* * * * *